(12) United States Patent
Kleinschmidt et al.

(10) Patent No.: US 12,364,814 B2
(45) Date of Patent: Jul. 22, 2025

(54) CONTACT SENSOR FOR MONITORING MEDICATION ADHERENCE

(71) Applicant: HIVE MEDICAL, INC., St. Louis, MO (US)

(72) Inventors: Glen Robert Kleinschmidt, Chicago, IL (US); Joseph Matthew Beggs, Saint Louis, MO (US); Jake Eshelman, Saint Louis, MO (US)

(73) Assignee: Hive Medical, Inc., Saint Louis, MO (US)

( * ) Notice: Subject to any disclaimer, the term of this patent is extended or adjusted under 35 U.S.C. 154(b) by 205 days.

(21) Appl. No.: 18/198,805

(22) Filed: May 17, 2023

(65) Prior Publication Data

US 2023/0302219 A1 Sep. 28, 2023

Related U.S. Application Data

(63) Continuation-in-part of application No. 16/846,012, filed on Apr. 10, 2020, now Pat. No. 11,684,715.

(60) Provisional application No. 62/832,058, filed on Apr. 10, 2019, provisional application No. 63/342,963, filed on May 17, 2022.

(51) Int. Cl.
*A61M 5/168* (2006.01)
*A61M 39/10* (2006.01)
*A61B 5/00* (2006.01)

(52) U.S. Cl.
CPC .... *A61M 5/16886* (2013.01); *A61M 5/16804* (2013.01); *A61M 39/10* (2013.01); *A61B 5/4833* (2013.01)

(58) Field of Classification Search
CPC ............ A61M 5/16831; A61M 5/1413; A61M 39/10; A61M 5/18668
USPC .......................................................... 285/93
See application file for complete search history.

(56) References Cited

U.S. PATENT DOCUMENTS

| | | |
|---|---|---|
| 3,876,234 A | 4/1975 | Harms |
| 5,429,614 A | 7/1995 | Fowles et al. |
| 7,727,194 B2 | 6/2010 | Nalagatla et al. |
| 8,747,348 B2 | 6/2014 | Yodfat et al. |
| 8,870,818 B2 | 10/2014 | Alderete, Jr. et al. |
| 9,039,659 B2 | 5/2015 | Hanson et al. |
| 9,452,255 B2 | 9/2016 | Tieck et al. |
| 9,533,092 B2 | 1/2017 | Gyrn |
| 9,752,914 B2 | 9/2017 | Levine |
| 10,293,119 B2 | 5/2019 | Caspers et al. |
| 10,857,287 B2 | 12/2020 | Damiano et al. |
| 11,684,715 B2 | 6/2023 | Beggs et al. |
| 2004/0036273 A1 | 2/2004 | McClary |

(Continued)

*Primary Examiner* — David Bochna
(74) *Attorney, Agent, or Firm* — Polsinelli PC

(57) ABSTRACT

Systems, devices, and methods described herein indirectly monitor a state of fluid flow by monitoring a state of connection of a medication delivery device. The system includes an enclosure, a contact sensor, and a controller. The enclosure can attach around at least a portion of an outer surface of the medication delivery device to enclose at least a portion of the outer surface therein. The contact sensor and controller are enclosed within the enclosure. The contact sensor can monitor a state of electrical connection. The controller is in communication with the contact sensor and can relay the state of electrical connection. The state of connection of the contact sensor corresponds to the state of connection of the medication delivery device.

29 Claims, 30 Drawing Sheets

(56) References Cited

U.S. PATENT DOCUMENTS

| | | |
|---|---|---|
| 2004/0140666 A1* | 7/2004 | Lin .......................... F17D 5/06 |
| | | 285/93 |
| 2007/0241119 A1* | 10/2007 | Durkin .................. A61M 39/02 |
| | | 340/603 |
| 2013/0177455 A1* | 7/2013 | Kamen ............. A61M 5/16831 |
| | | 417/313 |
| 2016/0015886 A1 | 1/2016 | Pananen |
| 2017/0059374 A1* | 3/2017 | DeKalb ............. A61M 5/16831 |
| 2017/0203860 A1* | 7/2017 | Py .......................... A61M 39/10 |
| 2018/0364086 A1* | 12/2018 | Farinella ........... A61M 5/16886 |
| 2019/0326012 A1 | 10/2019 | Witt |
| 2022/0001105 A1* | 1/2022 | Shmilovich ......... A61M 5/1413 |
| 2022/0125533 A1* | 4/2022 | Falb ...................... A61M 39/10 |
| 2022/0233264 A1* | 7/2022 | Klem ..................... A61B 34/74 |
| 2024/0139414 A1* | 5/2024 | Pieschnik .......... A61M 5/16886 |
| 2025/0018163 A1* | 1/2025 | Labib ................... A61M 39/10 |

\* cited by examiner

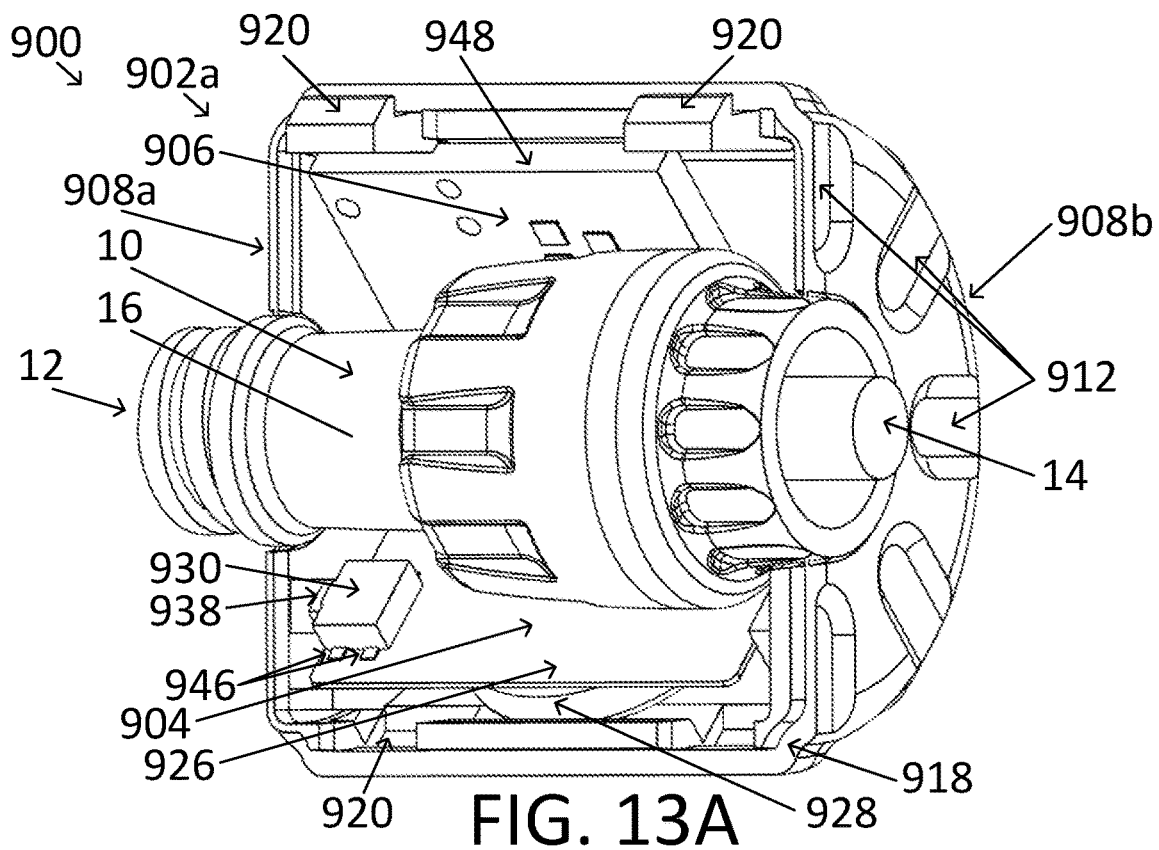
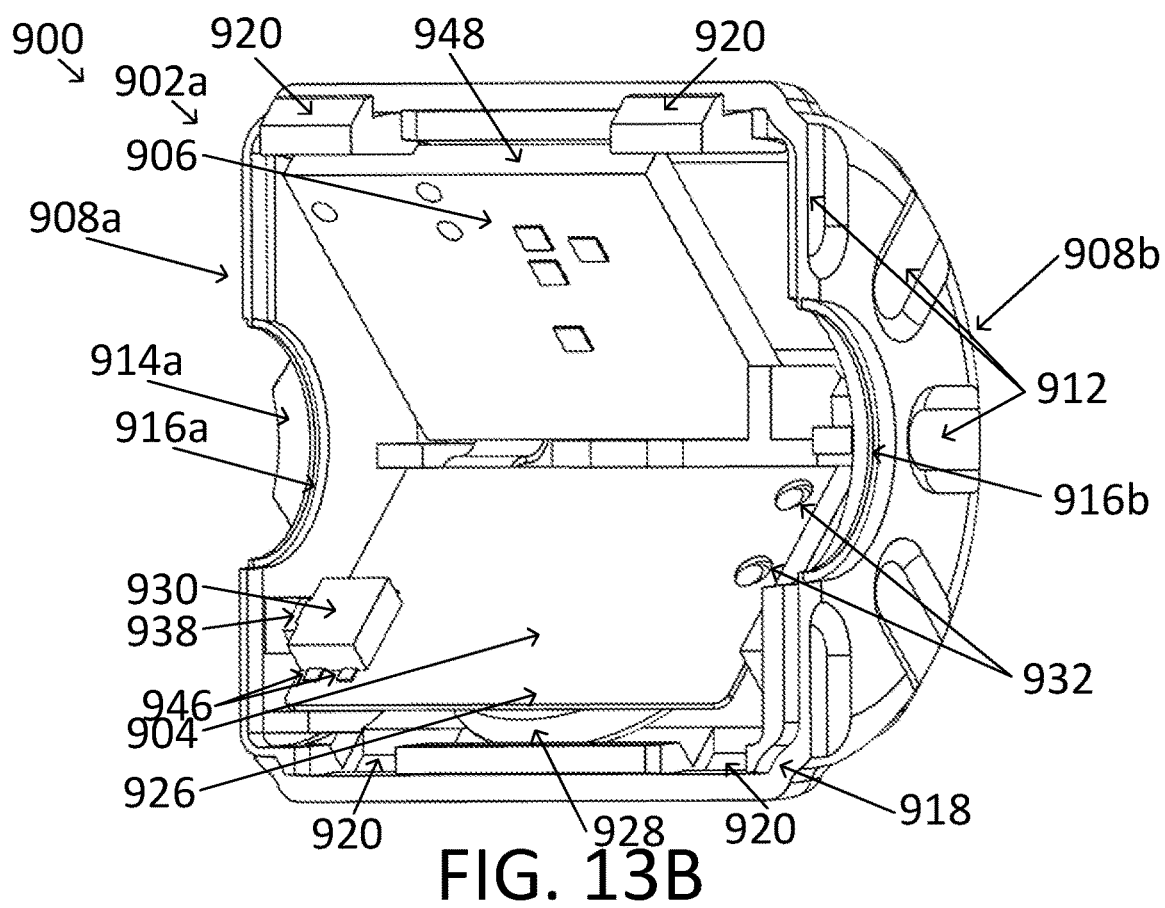

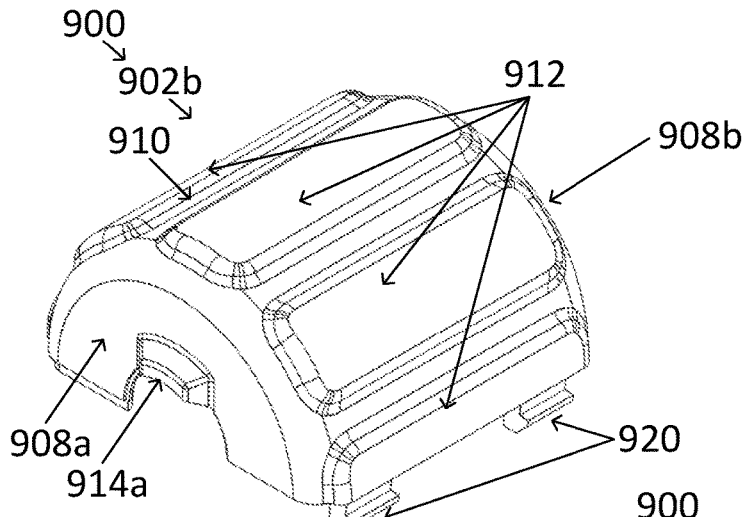
FIG. 15A
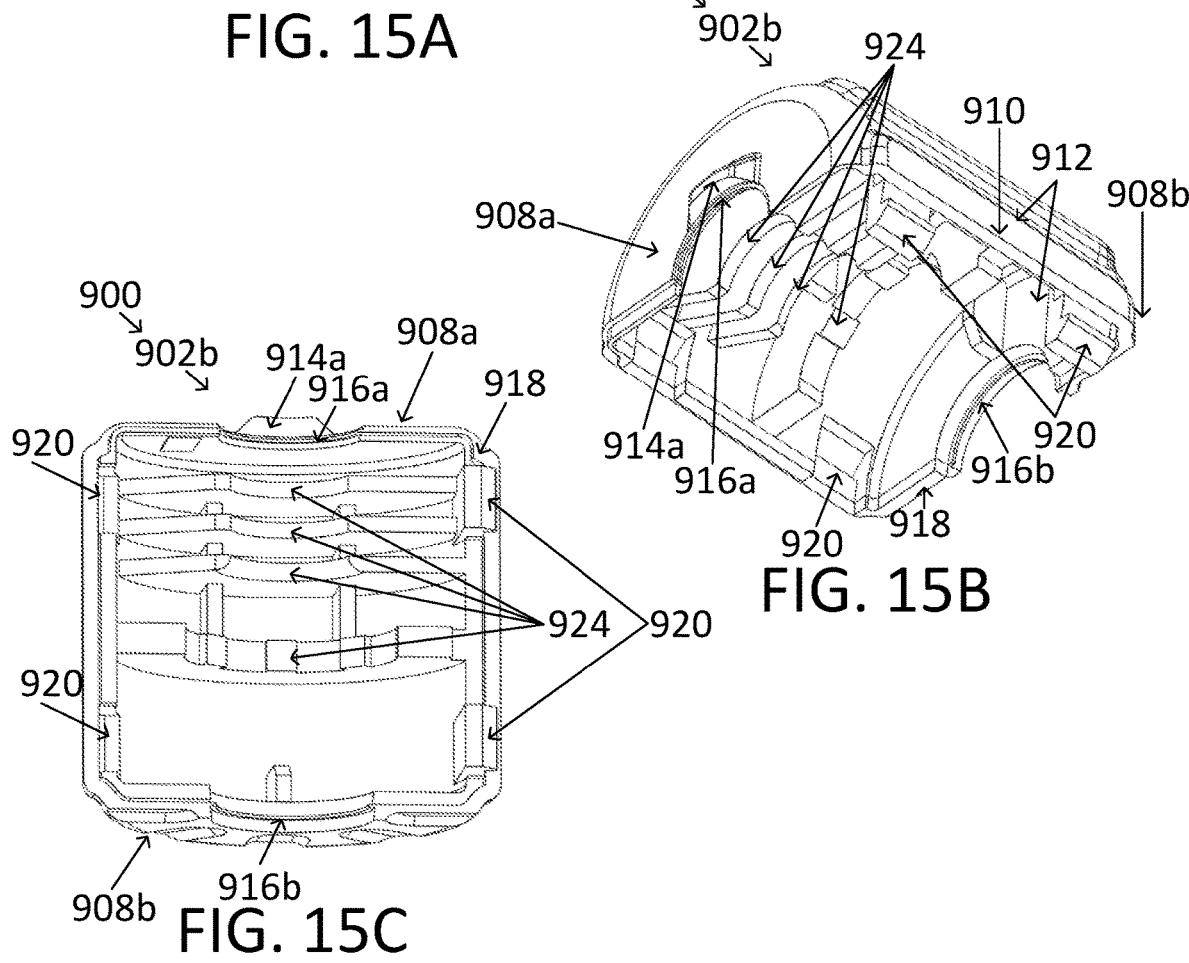
FIG. 15B
FIG. 15C

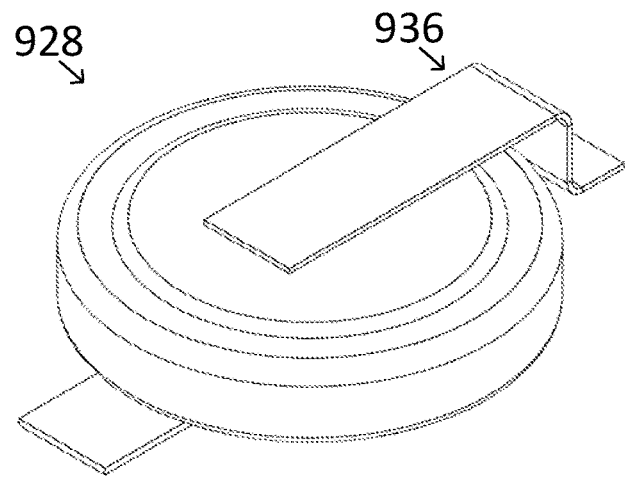
FIG. 18A
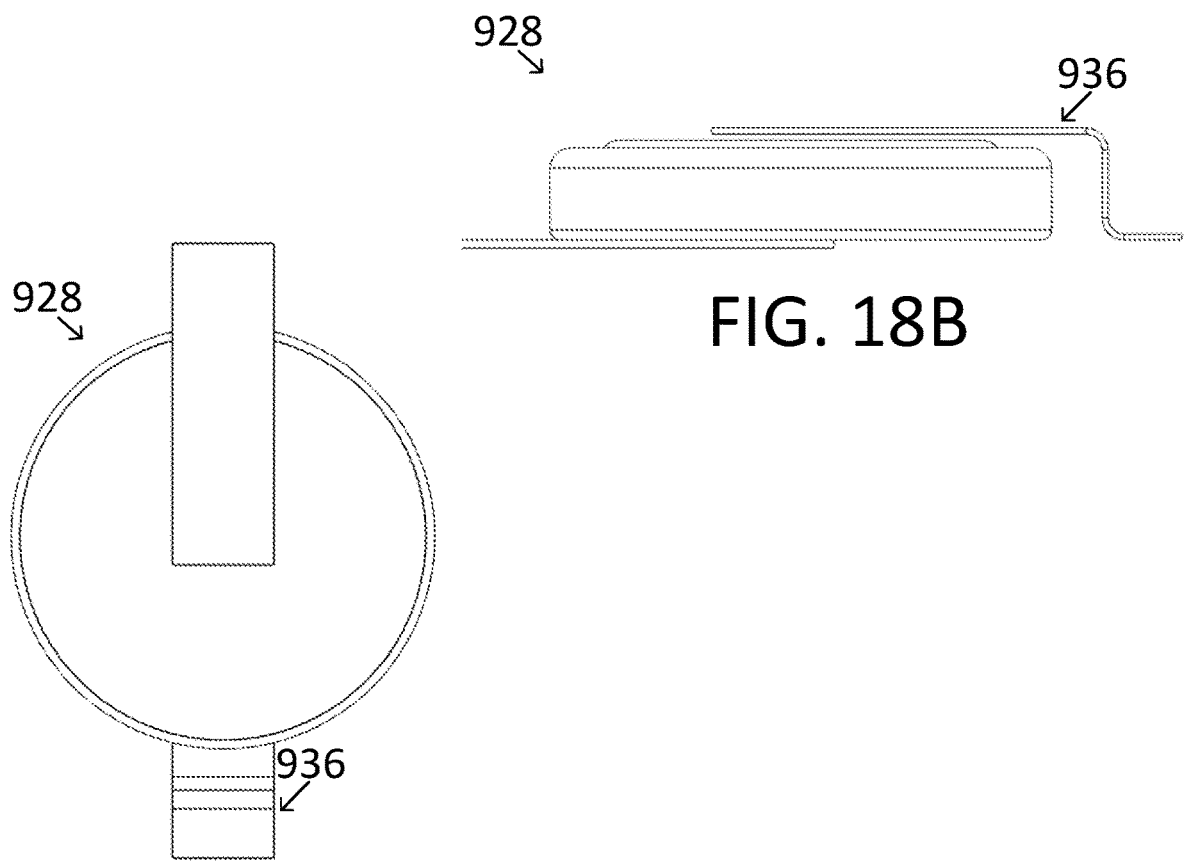
FIG. 18B
FIG. 18C

CONTACT SENSOR FOR MONITORING MEDICATION ADHERENCE

CROSS-REFERENCE TO RELATED APPLICATIONS

This application is a continuation-in-part of U.S. application Ser. No. 16/846,012, filed Apr. 10, 2020, which claims the benefit of U.S. Provisional Application No. 62/832,058 filed Apr. 10, 2019, and this application also claims the benefit of U.S. Provisional Application No. 63/342,963 filed May 17, 2022, each of which are hereby incorporated by reference in their entirety.

FIELD OF THE INVENTION

The present disclosure provides systems, devices, and methods to monitor a fluid flow path between a medication reservoir and a medication dispense assembly in a medication delivery device.

BACKGROUND OF THE INVENTION

In the medical field one of the largest challenges with at-home medication is the issue of non-adherence caused by patients, either advertently or inadvertently, not following their prescribed medication regimen. This non-adherence includes but is not limited to patients failing to take medication at the prescribed times of day, for the prescribed duration of time and/or for the prescribed number of times per day. Outpatient care is typically much less expensive than inpatient care, and as a result, healthcare providers have drastically increased the proportion of patients receiving outpatient care compared to inpatient care over the past few decades. However, with reduced oversight from providers (e.g., doctors and nurses), non-adherence has become a more prevalent problem. Therefore, a method to objectively monitor outpatient medication regimen adherence is useful.

Currently, the only consistent methods for dealing with outpatient non-adherence are with house visits and phone calls. The latter has limited effectiveness and both take time and resources that could be more efficiently allocated and administered. As the median age of people in the United States continues to increase the need for a system of monitoring patient adherence will also become more valuable. Conventional solutions have put the onus on the non-adherent patients to do extra work in order for these solutions to monitor adherence, but this is not effective because non-adherent patients typically do not go out of their way to follow extra directions.

SUMMARY OF THE INVENTION

Aspects of the present disclosure include a system and method for indirectly monitoring a state of fluid flow by monitoring a state of connection of a medication delivery device. The system includes an enclosure, a contact sensor, and a controller. The enclosure is configured to attach around at least a portion of an outer surface of the medication delivery device such that at least a portion of the outer surface of the medication delivery device is enclosed within the enclosure. The contact sensor is disposed within the enclosure and configured to monitor a state of electrical connection. The controller is disposed within the enclosure. The controller is in communication with the contact sensor and configured to relay the state of electrical connection. In some aspects, the state of electrical connection of the contact sensor corresponds to the state of connection of the medication delivery device.

In certain instances, the state of connection of the medication delivery device corresponds to the state of fluid flow. In certain instances, the state of connection of the medication delivery device corresponds to a state of connection of a medication flow pathway. In certain instances, the state of connection of the medication flow pathway corresponds to the state of fluid flow.

In certain instances, the system indirectly monitors the state of fluid flow without contacting any fluid within the medication delivery device. In certain instances, the enclosure encloses 360-degrees radially around a perimeter of the outer surface of the medication delivery device when the enclosure is attached thereto. In certain instances, the enclosure encloses less than 360-degrees radially around a perimeter of the outer surface of the medication delivery device when the enclosure is attached thereto.

In certain instances, the enclosure has a first end and a second end and the enclosure encloses a length along the outer surface of the medication delivery device when the enclosure is attached thereto. The length can be less than or equal to a distance between the first end and the second end of the enclosure. In certain instances, the enclosure encloses 360-degrees radially around a perimeter of the outer surface of the medication delivery device. In certain instances, the enclosure encloses less than 360-degrees radially around a perimeter of the outer surface of the medication delivery device.

In certain instances, the medication delivery device is a needleless connector. In certain instances, the outer surface is defined by a compressible sleeve within the needleless connector such that the system is integrated within the needleless connector. In certain instances, the outer surface is defined by an outer component of the needleless connector such that the system is external to the needleless connector. In certain instances, the outer surface is defined by an internal component of the needleless connector such that the system is internal to the needleless connector.

In certain instances, the wherein the medication delivery device is fluidly connected within a medication flow pathway that includes one or more of the following: a medication source, an injection site, an IV insertion line, an extension set, an extension line, a regulator, or an end piece.

In certain instances, the enclosure is configured to non-removably attach around at least a portion of the outer surface of the medication delivery device.

In certain instances, the enclosure includes a first portion and a second portion. The first portion can be configured to attach to the second portion in order to attach the enclosure around at least a portion of the outer surface of the medication delivery device.

In certain instances, the enclosure has a first end and a second end opposite the first end. The first end of the enclosure can be compressible such that at least a portion of first end is configured to compress towards the contact sensor when the medication delivery device transitions to a connected position. In certain instances, an actuator of the contact sensor is in communication with the first end of the enclosure. In certain instances, connecting the medication delivery device to a fluid flow path causes the first end of the enclosure to compress. Depressing the actuator can cause a change of the state of electrical connection of the contact sensor when the first end of the enclosure compresses.

In certain instances, the medication delivery device is a needleless connector and the enclosure is integrated with the needleless connector.

In certain instances, the enclosure has a first end and a second end opposite the first end. The first end can include one or more extrusions extending outward and configured to contact a surface of a connector when the medication delivery device is in a connected position.

In certain instances, the enclosure has a first end and a second end opposite the first end. The first end can include one or more extrusions extending inward and configured to contact a surface of the contact sensor when the medication delivery device is in a connected position.

In certain instances, the enclosure has a first end and a second end opposite the first end. The first end can define a first seal that abuts the outer surface of the medication delivery device and the second end can define a second seal that abuts the outer surface of the medication delivery device. The first seal and the second seal can each be water-tight.

In certain instances, the enclosure includes one or more structures configured to abut the outer surface of the medication delivery device. The one or more structures abutting the medication delivery device can inhibit translation and rotation of the medication delivery device with respect to the enclosure.

In certain instances, an outer surface of the enclosure includes one or more surface features, the one or more surface features being parallel to an axis of the enclosure and defining a gripping surface.

In certain instances, the device includes a battery disposed within the enclosure and in electrical communication with the contact sensor. The battery is configured to supply a current that flows through the contact sensor when the contact sensor transitions to a closed-circuit position.

In certain instances, the controller relays a change in the state of the electrical connection, wherein a change in the state of electrical connection corresponds a change in the state of fluid flow. In certain instances, the controller is configured to relay feedback to an authorized user, wherein the feedback includes if data was relayed by the controller, if the data matches a therapy regimen, if an action is suggested or a combination thereof.

In certain instances, the system includes an indicator configured to indicate a compliance status of the system. The indicator can be one or more of the following: a light integrated into the enclosure, a speaker disposed within the enclosure, a vibrator disposed within the enclosure.

BRIEF DESCRIPTION OF THE FIGURES

The description will be more fully understood with reference to the following figures, which are presented as various embodiments of the disclosure and should not be construed as a complete recitation of the scope of the disclosure, wherein:

FIGS. 13A-13B illustrate perspective views of a first portion of the enclosure, which houses the electronic components, with the needleless connector therein and with the needleless connector removed, respectively, according to one embodiment of the present disclosure.

FIGS. 15A-15C illustrate perspective views of a second portion of the enclosure, which contains internal structures to position the needleless connector, according to one embodiment of the present disclosure.

FIGS. 18A-18C illustrate a battery in a perspective view, side view, and bottom view, respectively, according to one embodiment of the present disclosure.

DETAILED DESCRIPTION

Figure 1:
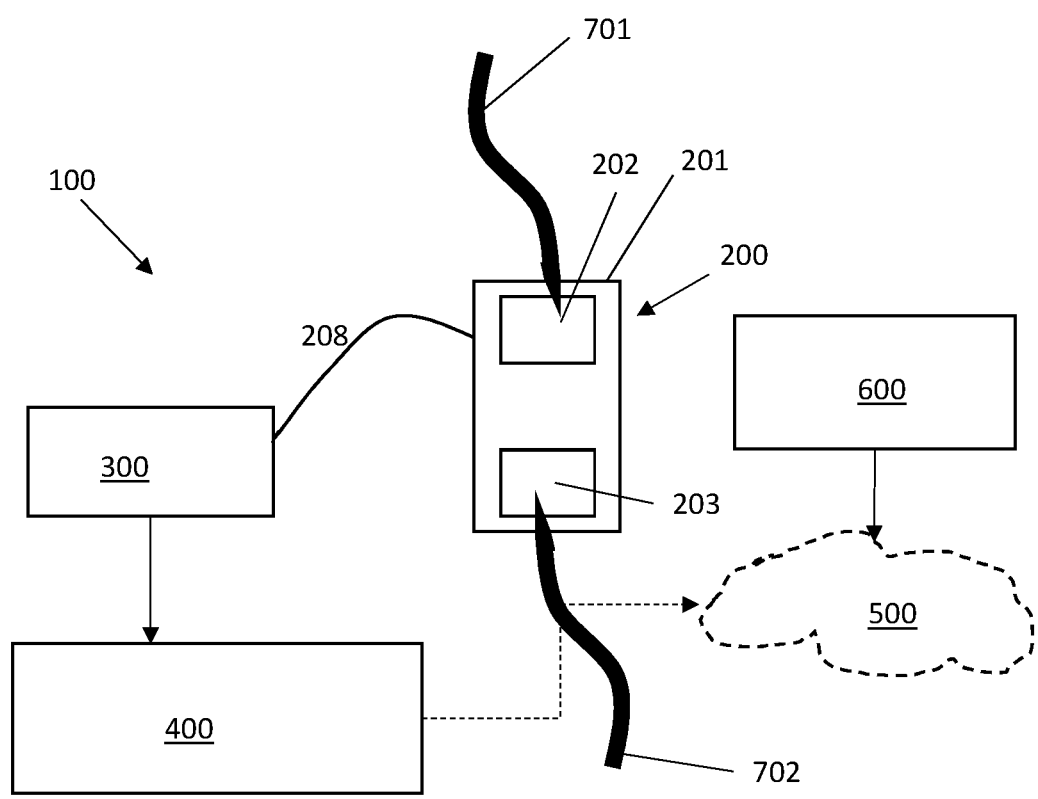
FIG. 1 illustrates a diagram of an aspect of a system in accordance with an aspect of the invention.

The systems, devices, methods, and computer program products for monitoring a fluid flow path will be understood from the accompanying drawings, taken in conjunction with the accompanying description. It is noted that, for purposes of illustrative clarity, certain elements in various drawings may not be drawn to scale. Several variations of the system are presented herein. It should be understood that various components, parts, and features of the different variations may be combined together and/or interchanged with one another, all of which are within the scope of the present application, even though not all variations and particular variations are shown in the drawings. It should also be understood that the mixing and matching of features, elements, and/or functions between various variations is expressly contemplated herein so that one of ordinary skill in the art would appreciate from this disclosure that the features, elements, and/or functions of one variation may be incorporated into another variation as appropriate, unless described otherwise.

Provided herein are systems, devices, methods, and computer program products for monitoring a fluid flow path of a medication for parenteral administration from a medication reservoir to a subject in need thereof. Parenteral administration can be subcutaneous, intramuscular, intraperitoneal, or intravenous administration.

In some aspects, systems disclosed herein monitor intravenous (IV) administration of medication by an IV administration device. In one aspect, the IV administration is an infusion of a medication. An IV infusion is a controlled administration of medication into your bloodstream over time. The infusion can be through standard IV lines. Standard IV lines are typically used for short-term needs. For instance, they may be used during a short hospital stay or in an outpatient setting to administer medication during surgery or to give pain medications, nausea medications, or antibiotics. A standard IV line can typically be used for up to four days. With standard IV administration, a needle can be inserted into a vein in the wrist, elbow, or the back of the hand. The catheter is then pushed over the needle. The needle is removed, and the catheter remains in your vein. All IV catheters are typically given in a hospital or clinic, or for outpatient IV therapy. Infusion can be pump infusion wherein a pump is attached to an IV line to send medication and a solution, such as sterile saline, into your catheter in a slow, steady manner. Pumps may be used when the medication dosage must be precise and controlled. Alternatively, infusion can be drip infusion. This method uses gravity to deliver a constant amount of medication over a set period of time. With a drip, the medication and solution drip from a bag through a tube and into the catheter.

An infusion can also be through a central venous catheter. Long-term medication treatment, such as chemotherapy or total parenteral nutrition, usually requires a central venous catheter (CVC) instead of a standard IV catheter. A CVC is inserted into a vein in your neck, chest, arm, or groin area. A CVC can stay in place for several weeks or even months. A CVC can be a peripherally inserted central catheter (PICC). A PICC has a long line that sends medication from the area of insertion, through your blood vessels, all the way to a vein near your heart. A PICC is typically placed in a vein above your elbow in your upper arm. A CVC can also be a tunneled catheter. With a tunneled catheter, medication can be sent directly into blood vessels in the heart. One end of the catheter is placed into a vein in the neck or chest during a short surgical procedure. The rest of the catheter is tunneled through the body, with the other end coming out through the skin. Medications can then be given into that end of the catheter. Additionally, a CVC can be an implanted port. Like a tunneled catheter, an implanted port inserts a catheter into a vein in the neck or chest. This device is also placed during a short surgical procedure. But unlike a tunneled catheter, an implanted port is located completely beneath the skin. To use this device, a healthcare provider injects medication through the skin into the port, which sends the medication into the bloodstream.

The systems, devices, methods, and computer program products allow for monitoring when and for how long the patient is using the apparatus for the parenteral administration of medication. Monitoring administration allows interested parties (e.g., medical professionals, patient caregivers, patient family and friends, etc.) be kept up to date on the patient's adherence. Practical uses for this information include but are not limited to: determining which patients need check-ups (e.g., in person, via telephone, via Internet such as instant messaging or video conference, etc.) to adjust their habits of usage, alerting physicians to patients who may be potentially abusing their medical devices, and/or tracking the non-adherence of patients, which would allow insurance companies and healthcare professional to determine which patients are more at-risk. One advantage of the systems and methods described herein includes providing objective verification of medication adherence of Outpatient Parenteral Antibiotic Therapy (OPAT) patients. The systems and methods described herein require minimal effort from patients, and this is particularly important for non-adherent patients. The systems, devices, and methods described herein also benefit from a simple and inexpensive design.

Figure 3:
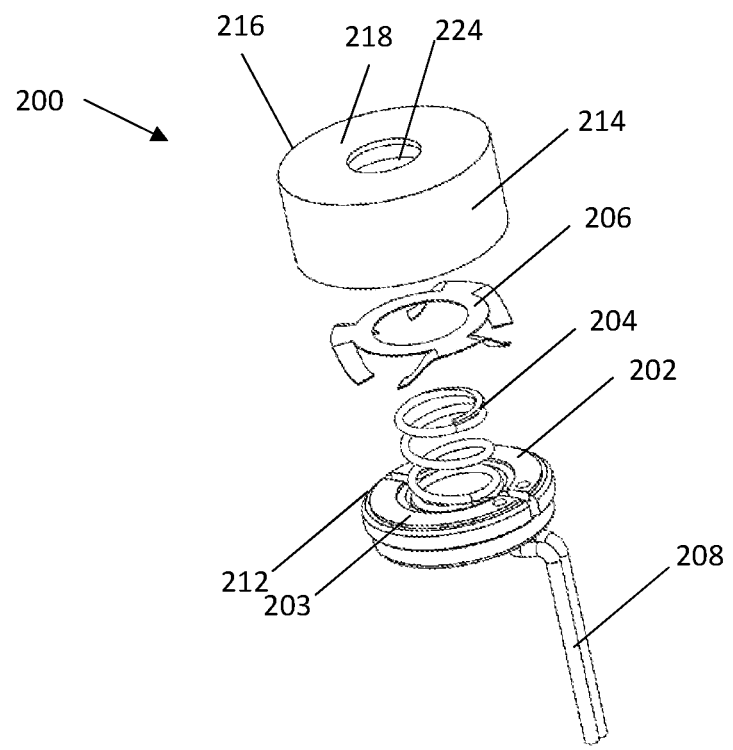
FIG. 3 is an exploded perspective view of an aspect of a contact sensor.
Figure 4:
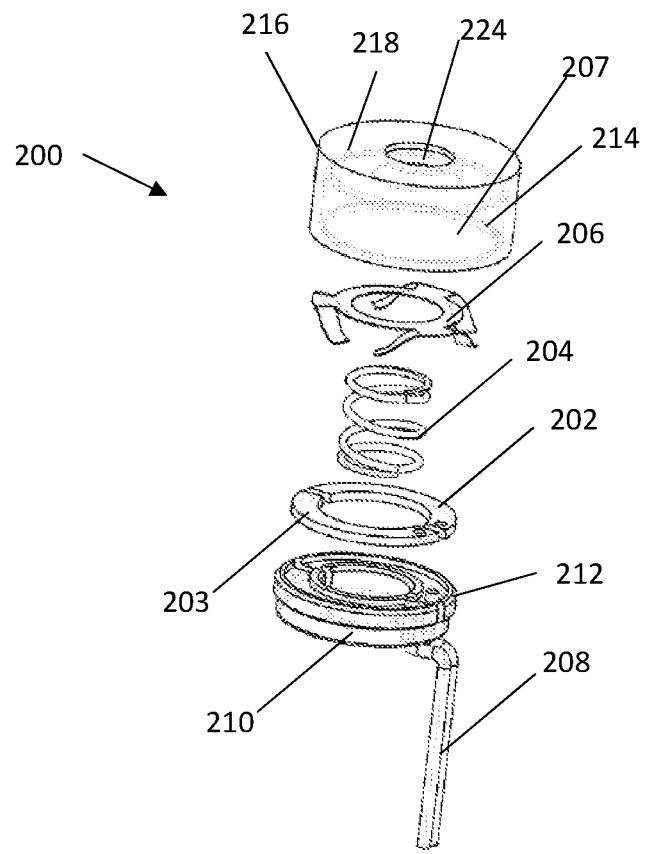
FIG. 4 is an exploded perspective view of an aspect of a contact sensor.

Referring to FIG. 1, one aspect of the system 100 is presented in accordance with an example in which a contact sensor 200 for attachment to a medication delivery device. The device can be removably attached to the medication delivery device. The electrical contact sensor 200 comprises an enclosure 201 comprising a first electrical contact 202, a second electrical contact 203, and a first spring 204 (shown in FIG. 3) operable to bias the first and second contacts from establishing an electrical connection. As shown in FIG. 1, system 100 further comprises a controller 300 in electrical communication with the contact sensor 200 through electrical wiring 208. A secondary device 400 may be in communication with the controller 300 of system 100. A cloud database 500 may also be in communication with the controller 300 or the secondary device 400 where one or more time events and/or states of the fluid flow path is stored for access by an individual of interest through an API 600. The individual can be the patient, or an individual monitoring the administration of the medication to the subject, such as a caretaker. Tubing 701 and 702 are shown attached to the contact sensor 200.

Figure 2:
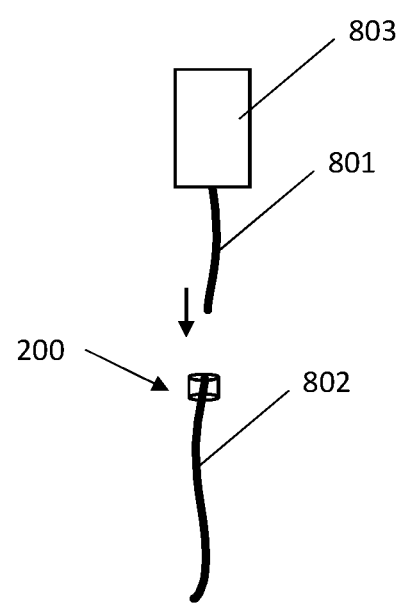
FIG. 2 is a diagram of an example of a contact sensor attached to a first section of an IV line at a connector before attaching the first section of the IV line with a second section of the IV line at the connector. A medication reservoir attached to the second section of the IV line is shown.

Referring to FIG. 2, the figure shows an example of a contact sensor 200 attached to a first end of a first section 802 of an IV line at a connector (not shown). A medication delivery device (not shown) is connected to a second end of the first section 802. Also shown is a second section 801 of an IV line. A medication reservoir 803 attached to the second section 801 of the IV line is shown. The figure shows the contact sensor and the IV lines before connecting the first and second sections of the IV line. The device and IV lines are shown before attaching the first section 702 of the IV line with the second section 801 of the IV line at the connector. The arrow shows the direction of the fluid flow path from the medication reservoir 803 to the medication delivery device.

Referring now to FIGS. 3-6, an aspect of the contact sensor 200 is shown. The electrical contact sensor 200 comprises an enclosure 201. The enclosure 201 comprises an elongated body 214 comprising a cavity, a proximal surface 216 comprising a top surface 218, a bottom surface 205, and an orifice 224 extending from the top surface 218 to the bottom surface 205. The body 214 comprises a distal opening 207. The enclosure 201 also comprises a support 210 comprising a distal surface 211, a proximal surface 212, a perimeter complementary to the inside perimeter of the enclosure, an orifice 213 extending from the distal surface 211 to the proximal surface 212 of the support 210. The orifice 213 is concentric with the orifice 224 in the body 214, forming a channel extending from the orifice 224 in the body 214 to the orifice 213 in the support 210. The support 210 is operable to be displaced along a longitudinal axis within the cavity of the body 214. In the aspect of the contact sensor 200 depicted in FIG. 2 and FIG. 3, the first electrical contact 202 and the second electrical contact 203 are attached to the proximal surface 212 of the support 210 in a shape operable to surround the orifice 213 in the support. The first spring 204 is shown, surrounding the channel and extending from the bottom surface 205 of the body 214 to the proximal surface 212 of the support 210. The spring 204 is operable to bias the support 210 from the bottom surface 205 of the body 214. The spring can be a compression spring, an extension spring, a torsion spring, a constant force spring, or a washer spring. In one aspect, the spring is a compression spring.

In the aspect of the contact sensor 200 depicted in FIGS. 3-6, the enclosure 201 further comprises an electrically conductive ring 206 attached to the bottom surface 205 of the body 214. The conductive ring 206 is operable to contact and establish an electrical connection between the first electrical contact 202 and second electrical contact 203 when a force applied to the body 214 and/or support 210 to connect the medication reservoir with the dispense assembly through the channel causes the support 210 to compress the first spring 204 and be displaced along the longitudinal axis of the enclosure 201. The formation of an electrical connection signals the connection of the medication reservoir with the dispense assembly and the formation of the fluid flow path between the medication reservoir and dispense assembly. In some aspects, the conductive ring 206 is a finger disk spring.

The electrical contact sensor 200 is attached at a connector. In some aspects, the medication delivery device further comprises a first section of tubing 801 comprising a first end and a second end, wherein the first end of the first section of tubing is attached to and in fluid communication with the medication reservoir, and a second section of tubing 802 comprising a first end and a second end, wherein the first end of the second section of tubing is attached to and in fluid communication with the medication delivery device, and wherein each of the second end of the first section of tubing and the second end of the second section of tubing comprise a connector for connecting the second ends of the sections of tubing, thereby forming a fluid flow path between the medication reservoir and the dispense assembly. In an aspect, the contact sensor is attached at a connector between the medication reservoir and the first end of the first section of tubing. In another aspect, the contact sensor is attached at a connector between the dispense assembly and the first end of the second section of tubing. In yet another aspect, the contact sensor is attached at the connector for connecting the second ends of the sections of tubing.

In some aspects, the contact sensor is removably attached to a connector. The contact sensor can be attached around the outside surface of the connector. Alternatively, the contact sensor can be attached within a housing of the connector. It should be noted however, that a contact sensor of the disclosure does not form a part of and is not in contact with the fluid flow path.

Connectors can be any fitting appropriate for use with a peritoneal medication delivery device, such as luer tapers.

The system further comprises a controller 300 in electrical communication with the contact sensor 200 through electrical wiring 208. As explained above, the state of the electrical connection is the presence or absence of the electrical connection. The controller 300 comprises an input controller operable to receive the state of the electrical connection communicated by the sensor and at least one processor operable and assign one or more event times. Each event time indicates the time of a change in the state of the connection.

The controller 300 can be operable to communicate the one or more event times to an individual. For instance, the controller 300 can further comprise an output component to indicate a time event to an individual. Alternatively, the controller 300 can communicate the one or more event times to a secondary device 400. For example, the output component can be a transmitter operable to communicate the one or more event times to a secondary device 400 wirelessly using a wireless communication protocol.

Figure 7:
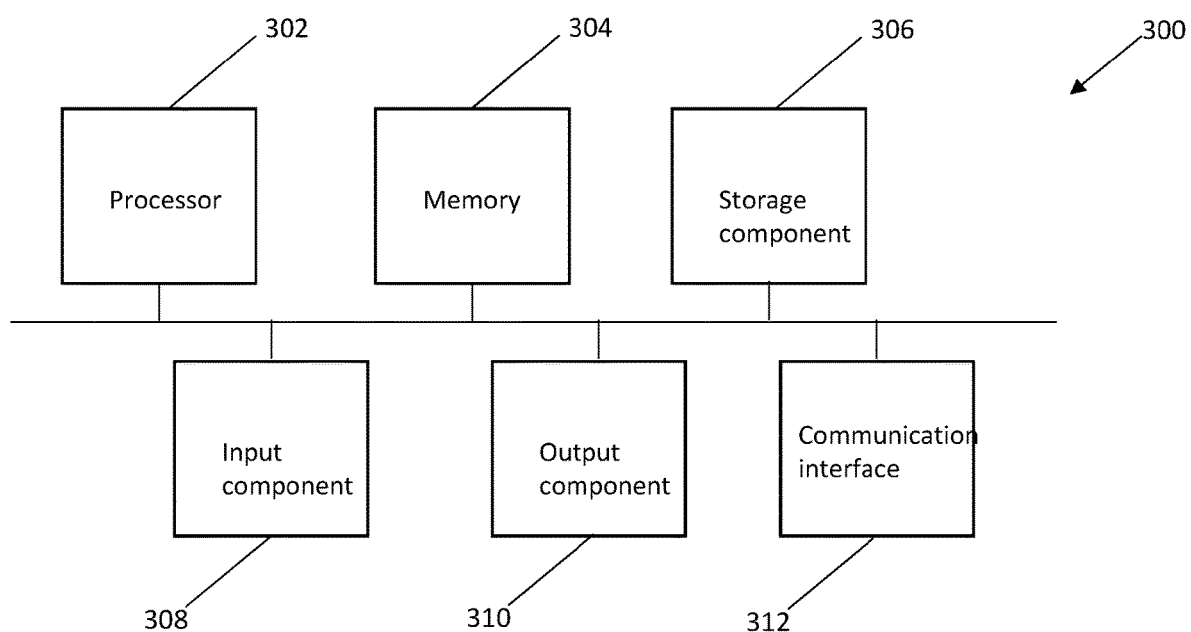
FIG. 7 is a diagram of an aspect of components of a controller.

Referring now to FIG. 7, FIG. 7 is diagram of components in accordance with an example controller 300. The controller 300 is provided by way of example, as the controller 300 can comprise other components, such as a transmitter, a computer monitor etc., that may be present for functioning of the controller in various aspects of the disclosure. Each block shown in FIG. 7 represents one or more component of controller 300. Furthermore, the illustrated order of blocks is illustrative only and the order of the blocks can change according to the present disclosure. Additional blocks may be added or fewer blocks may be utilized, without departing from this disclosure.

The example controller 300 shows the at least one processor 302. The controller 300 shown in FIG. 7 further comprise memory 304, storage component 306, input component 308, output component 310, and communication interface 312. A power source can provide power to the controller 300.

Memory 304 may include a random-access memory (RAM), a read only memory (ROM), and/or another type of dynamic or static storage device (e.g., a flash memory, a magnetic memory, an optical memory, etc.) that stores information and/or instructions for use by controller 300.

Storage component 306 may store information and/or software related to the operation and use of controller 300. For example, storage component 306 can include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

In addition to the input component 308 operable to receive the state of the electrical connection communicated by the sensor, the controller 300 can include addition input components that permits input by a user (e.g., a touch screen display, a keyboard, a keypad, a mouse, a button, a switch, a microphone, etc.).

Output component 310 may include a component that provides output information from controller 300 (e.g., a display, a speaker, one or more light-emitting diodes (LEDs), etc.).

Communication interface 312 may include a transceiver-like component (e.g., a transceiver, a separate receiver and transmission source, etc.) that enables controller 300 to communicate the one or more event times to a secondary device, such as via a wireless connection using a wireless communication protocol, a wired connection, or a combination of wired and wireless connections. A wired connection can include an Ethernet interface, an optical interface, a coaxial interface, an infrared interface, a universal serial bus (USB) interface, and/or the like. A wireless communication protocol can include an NFC communication, a Radio-frequency identification (RFID) communication, Bluetooth, LTE, ZigBee, LoraWAN, Wi-Fi, and/or the like.

The secondary device 400 can be a stationary computing device such as a desktop computer. Alternatively, the secondary device 400 can be mobile computing device such as a cellular phone (e.g., a smartphone or standard cellular phone), a portable computer (e.g., a tablet computer, a laptop computer, etc.), a wearable device (e.g., a watch, a pair of glasses, a lens, clothing, and/or the like), a personal digital assistant (PDA), a computing device with no user interface, and/or other like devices.

Figure 5:
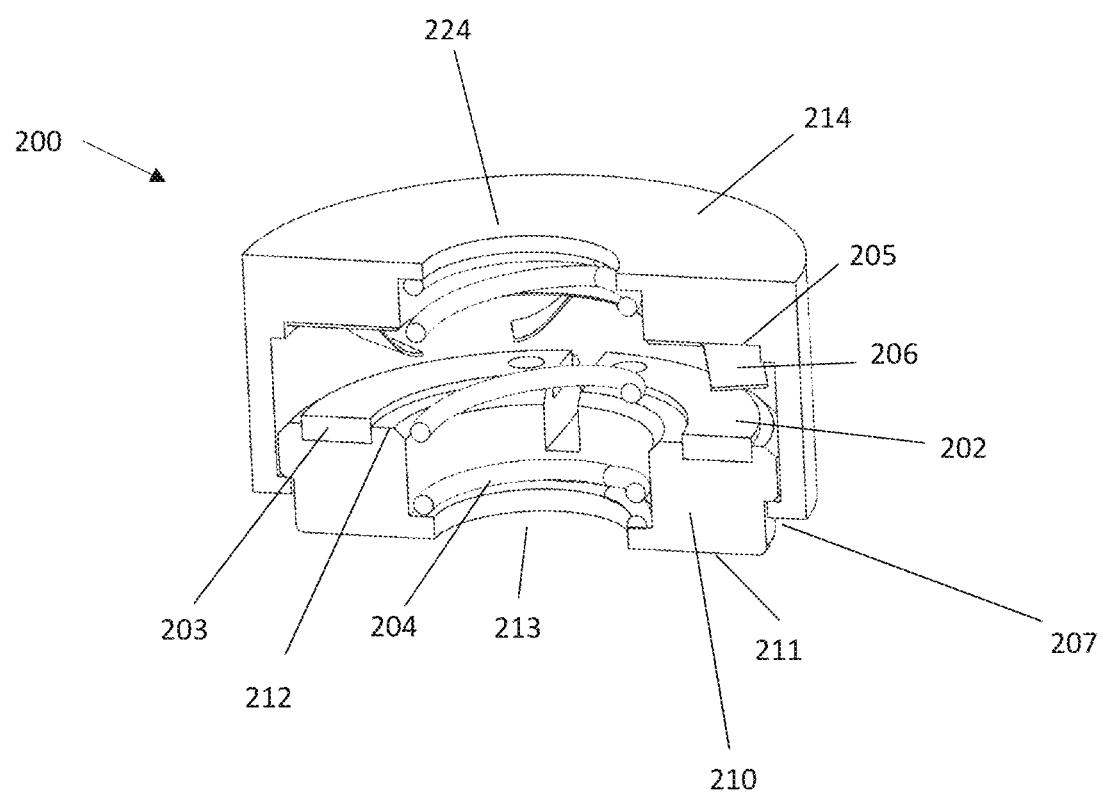
FIG. 5 is a perspective cross section view of the contact sensor.
Figure 6:
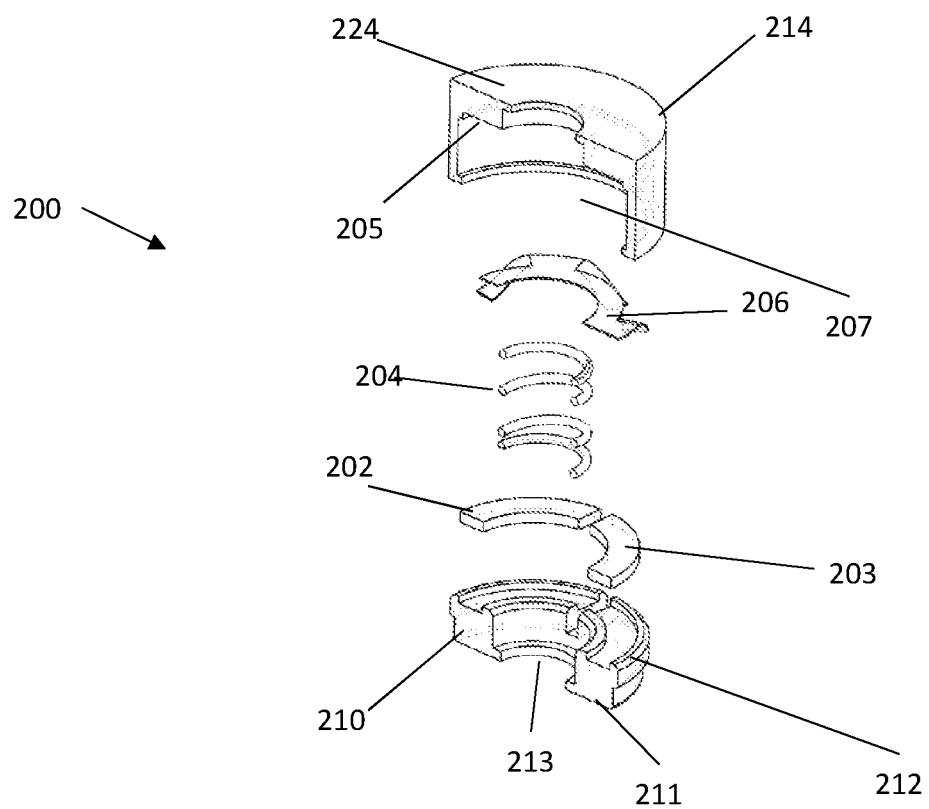
FIG. 6 is a perspective cross section exploded view of the contact sensor.
Figure 8:
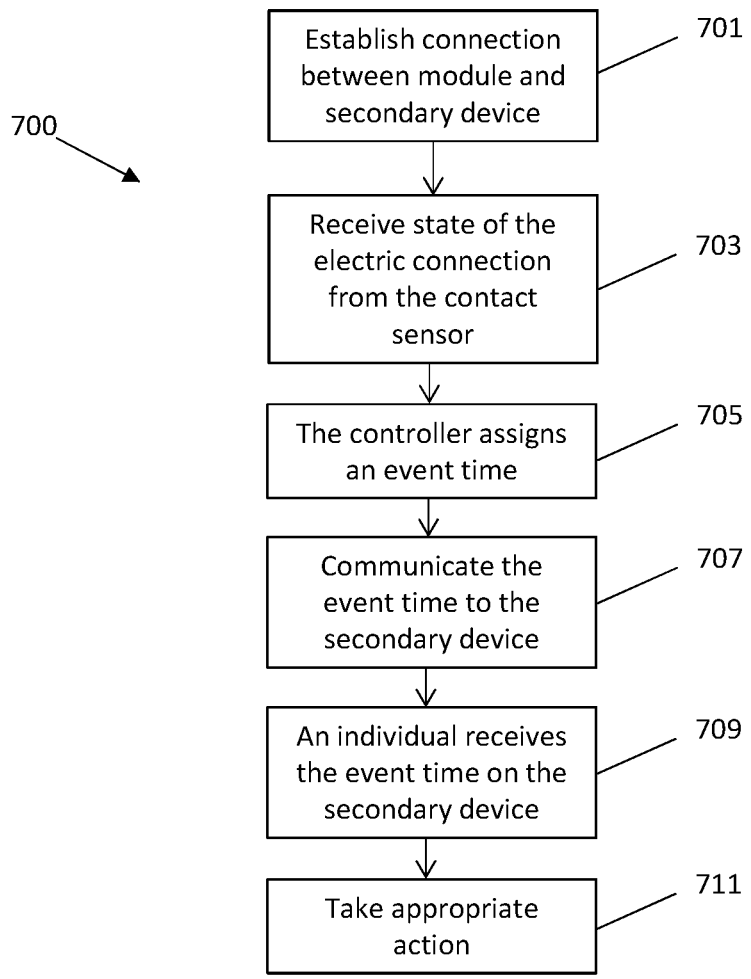
FIG. 8 is a flow chart of a method of use of the system.

Referring to FIG. 8, a flowchart is presented in accordance with an example method 700 of using the system 100. The method 700 is provided by way of example, as there are a variety of methods to use the system 100. Each block shown in FIG. 5 represents one or more processes, methods or subroutines, carried out in the example method 700. Furthermore, the illustrated order of blocks is illustrative only and the order of the blocks can change according to the present disclosure. Additional blocks may be added or fewer blocks may be utilized, without departing from this disclosure.

The example method 700 is a method for monitoring a fluid flow path of a medication for parenteral administration from a medication reservoir to a subject, and alerting an individual of interest of any change in the status of the fluid flow path. The example method 700 can begin at block 701. At block 701, a connection is established between the controller 300 and a secondary device 400. At block 703, the state of the electric connection is received by the controller from the contact sensor. The state of the electrical connection can be the presence or absence of an electrical connection. At block 705, the controller assigns an event time, wherein each event time indicates the time of a change in the state of the electrical current. At block 707, the controller 300 communicates the event time to a secondary device 400. At block 709, an individual receives the event time on the secondary device. For instance, the secondary device 400 can alert the individual when an even time is received. At block 711, the individual can take appropriate action based on the alert. For example, the individual can call instruct the patient to re-connect the medication device.

Figure 9:
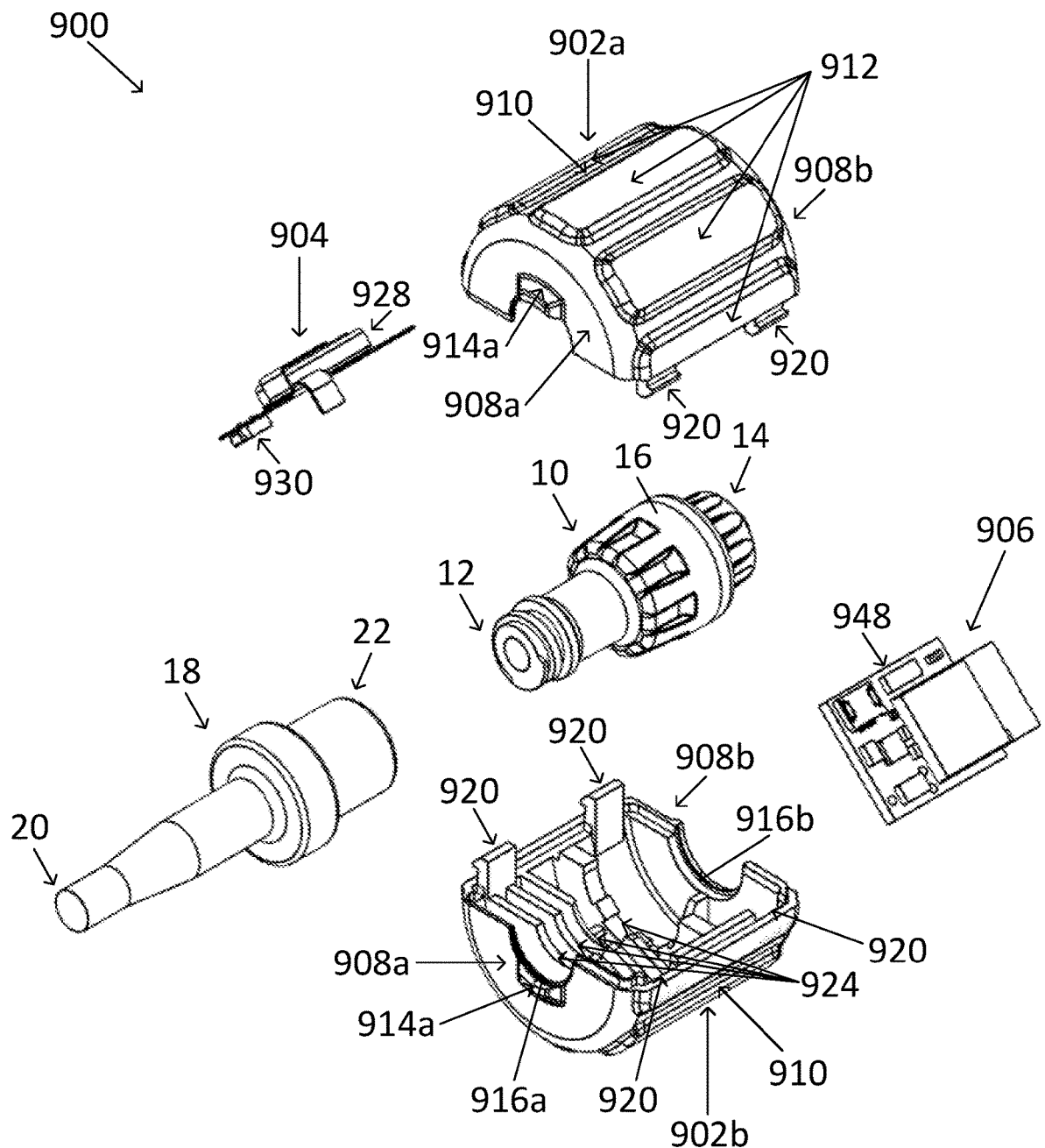
FIG. 9 illustrates a contact sensor assembly, in an exploded, perspective view, with a needleless connector and a pump connector, according to one embodiment of the present disclosure.
Figure 10:
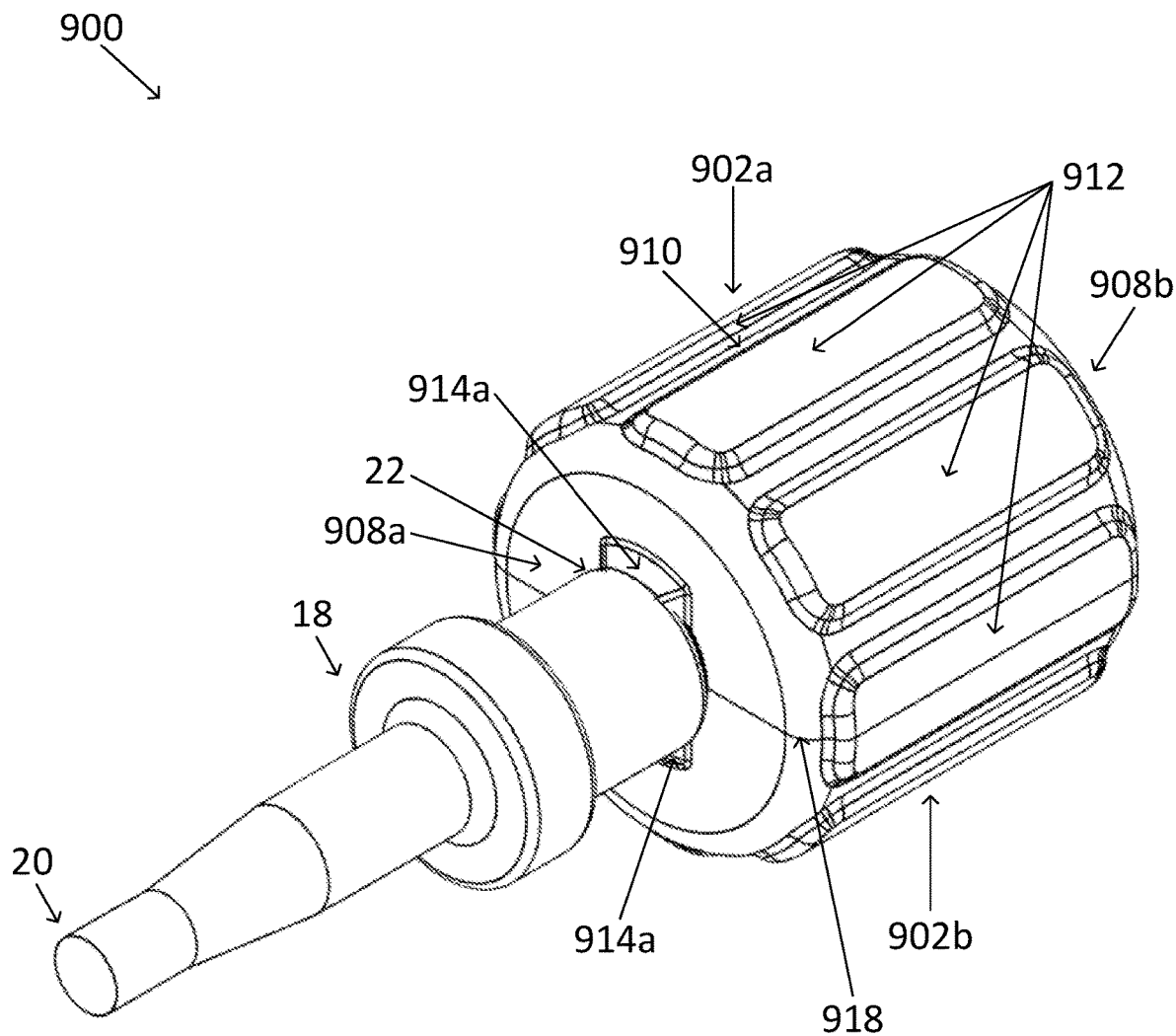
FIG. 10 illustrates the contact sensor assembly, in an assembled, perspective view, with the pump connector connected to the needleless connector.

Referring now to FIGS. 9-10, an electrical contact sensor assembly 900 is illustrated in a perspective view, according to one embodiment of the present disclosure. The electrical contact sensor assembly 900 (as illustrated for example in FIGS. 9-10) can have one or more same or similar features as the contact sensor 200 (as illustrated for example in FIGS. 3-6). Due to the same or similar features, certain descriptions provided for various components, elements, portions, etc., provided for the contact sensor 200 in FIGS. 3-6 can be generally applied to the same or similar components, elements, portions, etc., provided for the electrical contact sensor assembly 900 in FIGS. 9-10. In one embodiment, the electrical contact sensor assembly 900 includes an enclosure 902 (e.g., 902*a*, 902*b*) with internal components such as, for example, a flexible printed circuit board assembly 904 (referred to as flexible PCB assembly 904) and/or a rigid printed circuit board assembly 906 (referred to as rigid PCB assembly 906).

The electrical contact sensor assembly 900 is configured to be attached to (or coupled to) a medication delivery device, such as needleless connector 10, as illustrated for example in FIGS. 9-10. For example, as illustrated in FIGS. 9-10, the electrical contact sensor assembly 900 is not connected to the needleless connector 10 in the exploded view in FIG. 9 and is connected to the needleless connector 10 in the assembled view in FIG. 10. In some embodiments, the electrical contact sensor 900 is configured to be removably coupled to the medication delivery device. In other embodiments, the electrical contact sensor 900 is configured to be non-removably coupled (e.g., permanently affixed) to the medication delivery device.

It should be noted that although FIG. 10 illustrates the electrical contact sensor assembly 900 attached to a needleless connector 10, the electrical contact sensor assembly 900 disclosed herein is not limited to use with a needleless connector 10. For example, the electrical contact sensor assembly 900 can be configured to attach to any medication delivery device having a luer lock end, which includes but is not limited to a needleless connector 10 (as illustrated for example in FIG. 10), an extension set 24 (as illustrated for example in FIGS. 22A-22C), an end of an IV-line implant, an end of a medication source. In some examples, the electrical contact sensor assembly 900 can be configured to attach to any medication delivery device at any point (such as an end). For example, the medication delivery device can be connected to a female fitting 26, as illustrated for example in FIGS. 22A-22C.

The medication delivery device can be configured to fluidly couple to a fluid flow path (also referred to as a medication flow path or medication flow pathway). As a result, the electrical contact sensor assembly 900 can be attached to one or more sections of a medication flow pathway. When attached, the electrical contact sensor assembly 900 indirectly monitors the respective section of the medication flow path, as discussed below. The electrical contact sensor assembly 900 can detect the state of connection and/or a change in the state of connection of the fluid flow path of an IV line.

The electrical contact sensor assembly 900 is configured to indirectly monitor a state of fluid flow (e.g., flow, no flow, calculated rate of flow, duration of flow, time of flow change) by monitoring a state of connection (e.g., connected, not connected, moment of change of state) of the medication delivery device (e.g., needleless connector 10). In some aspects, the medication delivery device (e.g., needleless connector 10) is configured to be connected within a fluid flow path (also referred to as a medication flow path or medication flow pathway), such as illustrated for example in FIGS. 1-2 and in FIGS. 22A-22C. In some examples, the fluid flow path can extend from a medication reservoir to a dispense assembly, as previously discussed. In some aspects, the fluid flow pathway can include one or more of the following: a medication source (e.g., bags, pumps, syringes, drips), an injection site (e.g., Y-injection site, male or female luer lock injection site), an IV insertion line (e.g., PICC line, midline), an extension set, and extension line, a regulator (e.g., pinch claim, micro-regulating valve, stop cock, side clamp), an end cap (e.g., male or female luer cap, combi stopper, curos cap).

The electrical contact sensor assembly 900 includes a contact sensor 930 therein, as discussed below, which monitors a state of electrical connection (e.g., electrically connected, not electrically connected). The state of electrical connection of the contact sensor 930 can correspond to a state of connection (e.g., connected, not connected) of the medication delivery device (e.g., needleless connector 10). In some aspects, the state of connection of the medication delivery device corresponds to a state of connection (e.g., connected, not connected) of the medication flow pathway. In some aspects, the state of connection of the medication delivery device corresponds to a state of connection of the medication flow pathway. In some aspects, the state of connection of the medication delivery device corresponds to the state of fluid flow (e.g., flow, no flow) through the medication delivery device. In one example, a connected medication delivery device corresponds to flow of fluid therethrough and a disconnected medication delivery device corresponds to no flow therethrough.

Continuing with FIGS. 9-10, the electrical contact sensor assembly 900 can monitor the state of fluid flow without contacting fluid (if any) within (e.g., flowing through) the medication delivery device (e.g., medication flow pathway). In other words, in some aspects, the fluid flowing through the medication delivery device is not affected by (or otherwise contacted by) the electrical contact sensor assembly 900 attached thereto. In some aspects, the electrical contact sensor assembly 900 does not form part of the fluid flow path. In some aspects, fluid flowing through the fluid flow path (e.g., medication delivery device) does not contact the electrical contact sensor assembly 900.

In one embodiment, the electrical contact sensor assembly 900 includes an enclosure 902, 904, a flexible PCB assembly 904, and/or a rigid PCB assembly 906. As previously discussed, FIGS. 9-10 illustrate the electrical contact sensor assembly 900 being used with a needleless connector 10, and/or a pump connector 18. In some aspects, when the electrical contact sensor assembly 900 is assembled, the enclosure 902 encloses the flexible PCB assembly 904 and the associated components and the rigid PCB assembly 906 and the associated components. In some aspects, when the enclosure 902 is assembled around the medication delivery device, the enclosure 902 is watertight such that external moisture is inhibited from migrating into contact with the internal components.

In one embodiment, when the enclosure 902 (e.g., portion 902a, portion 902b) is connected to the medication delivery device (e.g., needleless connector 10), the enclosure 902 encloses at least a portion of the needleless connector 10. In some aspects, the enclosure 902 encloses all of the electrical components (e.g., flexible PCB assembly 904, rigid PCB assembly 906) of the system. In other embodiments, the electrical contact sensor assembly 900 can enclose one or more components, or sections of components, of the medication flow path. As non-limiting examples, such components can include: the entry site into the patient (which may include a catheter insertion site or an injection site), the connection between any two other sections (which may include tubing), the needleless connector, the medication source, and any section or component that modifies or controls or extends the flow of medication. In other embodiments, each of these components may also wholly or in part be connected to any number of sensors operatable to detect one or more states or changes in state of the medication flow path. In other embodiments, each component and/or sensor may, wholly or in part, each be contained by any number of enclosures or segments of enclosures.

In some aspects, the enclosure 902 (also referred to as the housing) of the electrical contact sensor assembly 900 includes two portions (i.e., portion 902a and portion 902b). In other embodiments, the enclosure 902 can include one, three, four, five, or six portions or components. In some examples, the enclosure 902 can include more than six portions. The enclosure 902 (or portions 902a, 902b of the enclosure 902) can protect any number of the internal components (e.g., flexible PCB assembly 904, rigid PCB assembly 906, contact sensor 930) from any number and/or variations of: physical forces, particulates, and from moisture. Moisture sources may include precipitation, humidity, fog, and ice.

The electronic components (e.g., flexible PCB assembly 904, rigid PCB assembly 906, contact sensor 930) of the electrical contact sensor assembly 900 function to detect the state and/or change of state, convert this into an electrical signal, and then store and share this data to any number of authorized recipients, with different degrees of granularity if so desired. In other embodiments, any number of sensors can by themselves, or in collaboration with any other number of sensors, detect, save and share any number of signals, each of which may be sent to uniquely specific ranges of authorized individuals, with different desired degrees of granularity.

In one embodiment, the detectable and transmittable electrical signal can represent a change in the connection (e.g., change in the connection between the female end of a needleless connector and the male end of the medication source). In other embodiments, the electrical signals can correspond to various other states and/or changes of states of the medication flow path (which may or may not be indicated by a change of connectivity between two or more segments of the fluid flow path). As non-limiting examples, other states can include: the amount of medication still to be delivered, the rate of medication delivery, the state of connection between any two or more components of the medication flow path, the presence or absence of flow in any number of sections of the medication flow path, the environments in which any number of sections of the IV fluid flow path exist, the identification of the fluid present within any number of sections of the medication flow path, or the orientation (and whether or not that orientation is deemed to be safe and./or proper) of any number of parts of the medication flow path.

The electrical contact sensor assembly 900 can include a first controller that is in communication with the contact sensor 930 which is either connected to the first PCB 904, or via a connection to a second PCB 906. In other embodiments, any number of controllers can be in communication with any number of PCBs, which may be classified as flexible, stiff or otherwise. The electrical contact sensor assembly 900 can include one or more contact sensors 930 and one or more power sources connected and/or in communication with the one or more PCBs 904, 906.

A secondary one or more devices (gateways or components of the gateway) can be in communication with the one or more controllers of the system for the purpose of sending and/or sharing and/or receiving and/or modifying any number of data points. One or more cloud databases can also be in communication with the controller and/or the one or more secondary (gateway) devices where one or more time events and/or states, or changes of either, of the fluid flow path is detected and stored for access by or shared to an individual of interest through one or more APIs. The individual can be the patient, an individual monitoring the administration of the medication to the subject, such as a caretaker, or any other person(s) authorized to view any part of this data.

Figure 11:
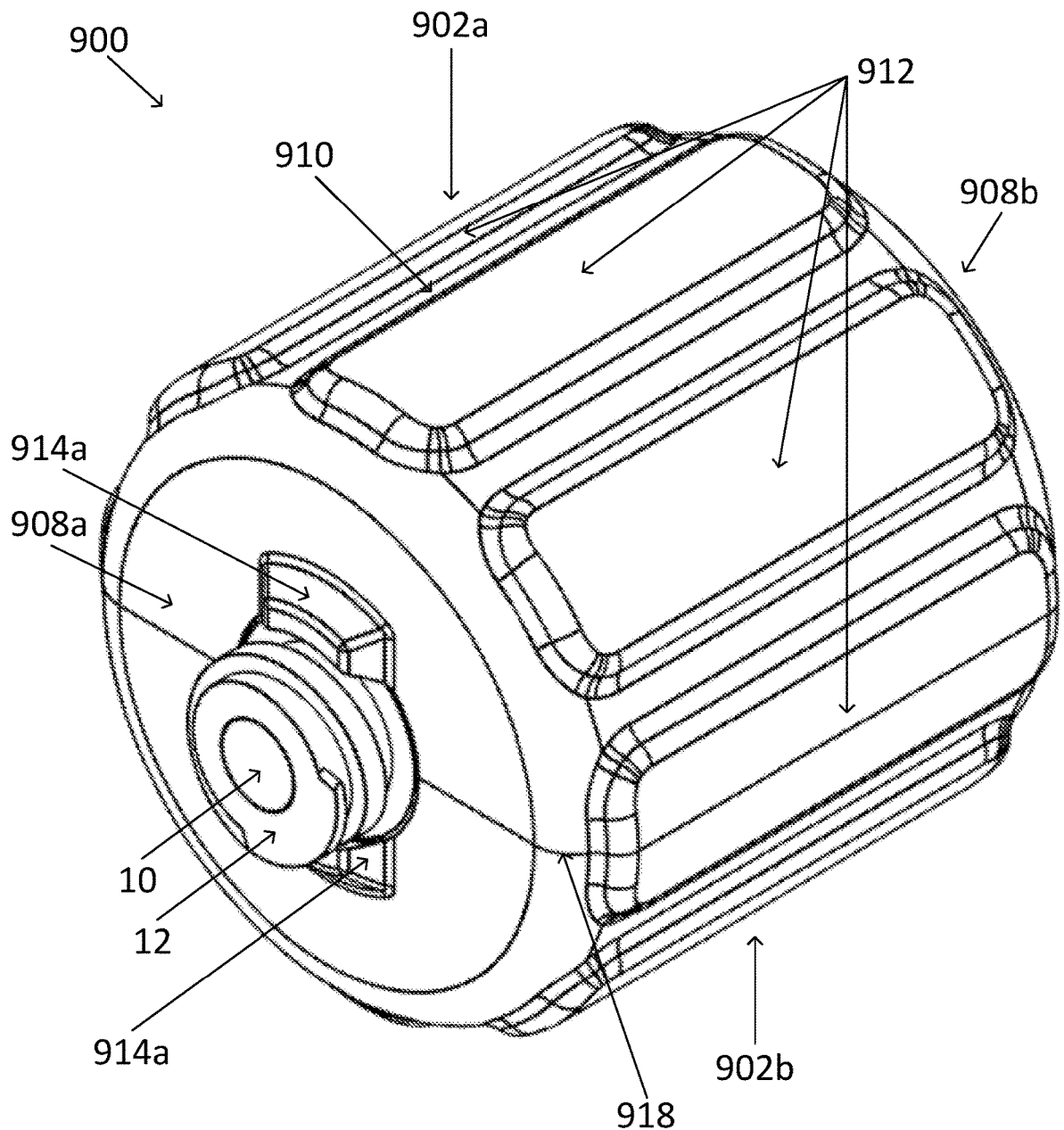
FIG. 11 illustrates the example contact sensor assembly in a perspective view with the needless connector therein.
Figure 12:
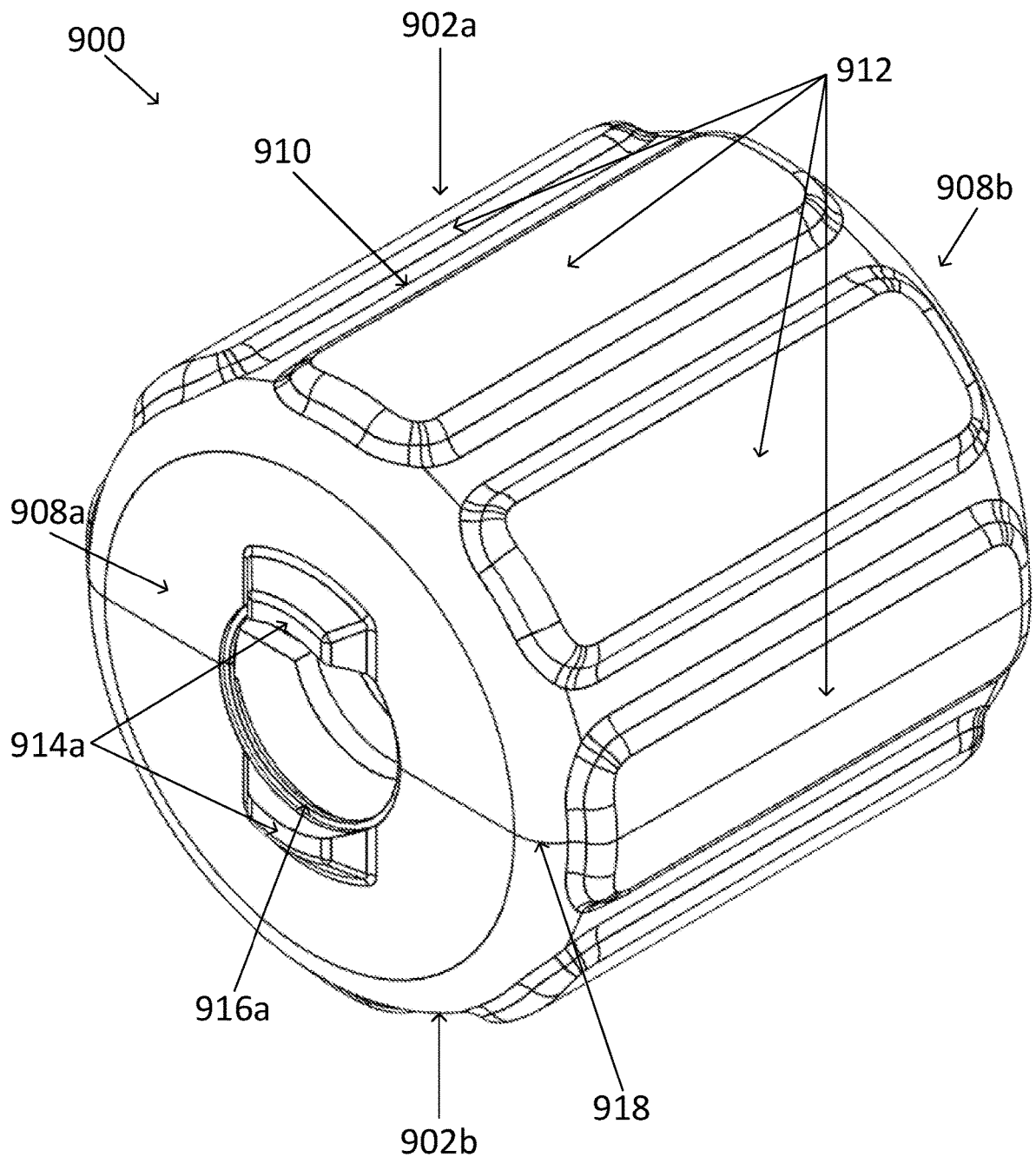
FIG. 12 illustrates the example contact sensor assembly in a perspective view with the needleless connector removed.

Referring now to FIGS. 11-12, one aspect an enclosure 902 (e.g., 902a, 902b) of an electrical contact sensor assembly 900 is illustrated in perspective views. In FIG. 11, the electrical contact sensor assembly 900 is shown with a needleless connector 10 but without the pump connector 18 (as illustrated for example in FIGS. 9-10). In FIG. 12, the electrical contact sensor assembly 900 is shown without the needleless connector 10. The enclosure 902 is configured to enclose at least a portion of a medication delivery device (e.g., needleless connector 10), when the enclosure 902 is attached thereto. As discussed previously, the medication delivery device can be part of an IV fluid system. In some aspects, the enclosure 902 can be printed (e.g., 3D printed) or molded (e.g., injection molded).

In some embodiments, the enclosure 902 includes portion 902a and portion 902b, which are configured to couple (e.g., snap, fit, lock) together to form the enclosure 902. In some aspects, the portions 902a, 902b can be removably coupled together to form the enclosure 902. In other aspects, the portions 902a, 902b can be non-removably coupled (e.g., permanently affixed) together to form the enclosure 902. In some aspects, the enclosure 902 forms a generally cylindrical shape when fully connected/sealed. In other embodiments, the enclosure 902 can include any number of parts or portions, which together can form any 3-D shape, which separately and/or in any number of combinations with other parts, work to cover, contain, orient, stabilize and/or otherwise mechanically optimize one or more sections of the IV fluid pathway(s) and/or sensor(s).

The enclosure 902 has a first end 908a and a second end 908b opposite the first end 908a and a shell 910. In some aspects, the enclosure 902 is generally cylindrical in shape, such that the first end 908a is a first base, the second end 908b is a second base, and the shell 910 defines a generally curvate surface. In some aspects, the first end 908a and/or the second end 908b define a generally planar surface that, when the enclosure 902 is attached to the medication delivery device (e.g., needleless connector 10), the first end 908a and/or the second end 908b are generally perpendicular to a longitudinal axis of the medication delivery device. In some aspects, the shell 910 defines a surface that, when the enclosure 902 is attached to the medication delivery device, the shell 910 is generally parallel to the longitudinal axis of the medication delivery device.

The enclosure 902 can include one or more surface features 912, which increase the ease of grip on and application of force to the enclosure 902. In some embodiments, as illustrated for example in FIGS. 9-10, surface features 912 (e.g., by addition) are on the shell 910 of the enclosure 902. In some aspects, the surface features 912 (e.g., by addition) are part of the shell 910 and the longitudinal axis of the surface features 912 are generally parallel to the longitudinal axis of the enclosure 902. In some embodiments, as illustrated for example in FIGS. 13A-13B, surface features 912 (e.g., by subtraction) are on the second end 908b of the enclosure 902. In other embodiments, these surface features 912 can be on any external face of the enclosure 902, and can include any other number, shape or variety of extrusion, and combination in shape or variety. The surface features 912 can be formed by addition (material is added to the surface of the enclosure 902) and/or by subtraction (material is removed from the surface of the enclosure 902).

Continuing with FIGS. 11-12, in some aspects, one or more portions of the enclosure 902 (e.g., first end 908a, second end 908b) are configured to move (or deflect) in response to the application of force. For example, when force is applied to the first end 908a and/or second end 908b, at least a portion of the first end 908a and/or second end 908b can compress inward (e.g., along a longitudinal axis and towards the center of the enclosure 902). When force is removed from the first end 908a and/or second end 908b, the portion of the first end 908a and/or second end 908b can rebound outward (e.g., to the original position). As discussed below, the first end 908a and/or second end 908b can be in communication with the contact sensor 930, as illustrated for example in FIGS. 13A-13B and discussed below, such that the position (e.g., compressed, not compressed) of the first end 908a and/or second end 908b corresponds to the state of electrical connection (e.g., electrically connected, not electrically connected) of the contact sensor 930.

The enclosure 902 (e.g., first end 908a, second end 908b) can include one or more extrusions 914 (e.g., 914a, 914b). The extrusions 914 can be a first point of contact to induce mechanical compression of the enclosure 902. In other words, the extrusion 914 can transfer force in the same direction of compression to one or more components (e.g., contact sensor 930) within the enclosure 902. In other embodiments, these extrusions 914 may take any other shape, such as bulbs, mounds, or stick-like extrusions. In other embodiments, as illustrated for example in FIGS. 23A-23B, the extrusion 2314 (e.g., 2314a) can be generally circular in shape around the opening that receives the medication delivery device (e.g., needleless connector 10). Moreover, other embodiments can include more than two extrusions 914 and/or may include the extrusions 914 in different configurations on the enclosure 902. The extrusions 914 can induce/direct a mechanical force and/or movement (including but not limited to pressure, compression and/or extension) in any number of desired directions. For example, in another embodiment, a force could be applied at a 90-degree angle to the face of contact, and the design of the enclosure could result in force being dispersed in a 45-degree angle to the face of contact.

In some embodiments, the extrusions 914 extend laterally outward from the first end 908a and/or second end 908b, as illustrated for example in FIGS. 11-12. In this configuration, the extrusions 914 provide a point of contact when a device (e.g., pump connector 18) is connected to the medication delivery device (e.g., needleless connector 10). For example, as the pump connector 18 is advanced (e.g., rotated about the threads) to fluidly couple the pump connector 18 to the needleless connector 10, a surface of the pump connector 18 contacts the extrusions 914 such that the first end 908a of the enclosure 902 begins to compress inward before the pump connector 18 is tightened or otherwise completely advanced. In some embodiments (not illustrated), the extrusions 914 extend laterally inward from the first end 908a and/or second end 908b, In this configuration, the extrusions 914 provide a point of contact when a device (e.g., pump connector 18) is connected to the medication delivery device (e.g., needleless connector 10). For example, as the pump connector 18 is advanced (e.g., rotated about the threads) to fluidly couple the pump connector 18 to the needleless connector 10, a surface of the pump connector 18 contacts the first end 908*a* of the enclosure 902 and advances the extrusions 914 inward as the first end 908*a* begins to compress inward. In some aspects, the inward-facing extrusions 914 can directly contact the contact sensor 930 (e.g., actuator 938). In this manner, compression of the first end 908*a* of the enclosure 902 causes compression of the actuator 938 of the contact sensor 930.

In some embodiments, the first end 908*a* and second end 908*b* of the enclosure 902 each define a seal 916 (e.g., 916*a*, 916*b*). Each seal 916 can abut the outer surface of the medication delivery device, such as the outer surface 16 of the needleless connector 10, when the enclosure 902 is attached to the medication delivery device. In some examples, each seal 916 is integrally formed with the respective first end 908*a* and second end 908*b*. In other examples, each seal 916 is a separate component, such as for example an O-ring (such as seals 2316*a*, 2316*b* as illustrated for example in FIGS. 23A-23B). In some aspects, each seal 916 inhibits ingress (e.g., is watertight) when the enclosure 902 is attached to the medication delivery device.

In some aspects, the enclosure 902 includes a lip with a sloping shape on the internal edges of the enclosure 902 (where the medication delivery device, such as a needleless connector 10, passes through the enclosure 902) that acts as both a liquid sealant once the needless connector 10 is inserted, and/or as a stabilizer for the needleless connector 10, without impeding the motion of the needless connector 10 when it is connected to other parts of the IV fluid path or otherwise handled. In other embodiments, the lip may include another shape or style, such as but not limited to: gradual slope or stair-shaped.

In one embodiment, the first end 908*a* and/or second end 908*b* of the enclosure 902 are configured to be compressible by an external force such that the first end 908*a* and/or second end 908*b* can be compressed from an original position to a compressed position. Then, the first end 908*a* and/or second end 908*b* can completely (or nearly) return to its original position once force is no longer applied. When compressed, the first end 908*a* and/or second end 908*b* can transfer mechanical force to the contact sensor 930 inside the enclosure 902. This can be accomplished by the first end 908*a* and/or second end 908*b* being sufficiently thin and flexible at the point of contact. In other embodiments, any number and any location of the enclosure 902 can be designed as a point of contact for a mechanical stimulation and/or transfer of mechanical force to stimulate and/or operate one or more contact sensors 930. This can be accomplished by multiple means, including but not limited to: specifically designing sections of the enclosure 902 to be varying degrees of thickness, allowing physical force to influence material on either side of contact, allowing for any dimension(s) of movement of any number of parts of the enclosure 902, or any torsion of the enclosure 902. For example, a section of the enclosure can be designed to operate a contact sensor 930 in response to a rotation of one part of the enclosure 902, and this section of the enclosure can return to its previous location/condition once it is released and/or there is no longer force keeping it in place.

In one embodiment, the first end 908*a* contains two extrusions 914*a* to aid in the transfer of force to the contact sensor 930. In other embodiments, there can be zero extrusions, one extrusion, or more than two extrusions, which can also take other forms, including but not limited to divots, switches and tabs, that can be placed/located on any location of the system and in any combination with any number of other extrusions. One or more contact sensors 930 can also be located in, under or integrated with any number of these extrusions 914.

In one embodiment, some point(s) of connection/sealing between the portions 902*a*, 902*b* of the enclosure 902 is along the cylindrical face. In other embodiments, there may be any number of connection points in any number of locations. For example, the point at which the enclosure portions 902*a*, 902*b* are connected/sealed could be one or both of the two circular bases and/or the curved surface of the cylindrical body.

In some embodiments, the electrical contact sensor assembly 900 can include one or more indicators (e.g., vibrators, lights, speakers, etc.). The indicator can be configured to indicate a compliance status (e.g., compliance, non-compliance), which can correspond to a medication delivery plan (also referred to as a medication delivery schedule). In this manner, the indicator can promote and/or encourage a specific usage by the user (e.g., patient). For example, the vibrator can vibrate to indicate a compliance status, a light can illuminate to indicate a compliance status, and/or a speaker can provide an audible sound to indication a compliance status. In one example, the enclosure 902 includes a light that indicates compliance (e.g., by flashing a "green" color) and/or non-compliance (e.g., by flashing a "red" color).

Referring to FIGS. 13A-13B, the enclosure 902 (e.g., portion 902*a*) of the electrical contact sensor assembly 900 is illustrated with the internal electronics therein. The medication delivery device (e.g., needleless connector 10) is illustrated in FIG. 13A and removed in FIG. 13B. The enclosure 902 forms a housing that contains and protects the contact sensor 930 and circuits. In one embodiment the first portion 902*a* of the enclosure 902 houses the electronic components. In other embodiments, the electronic components can be disposed within other portions of the enclosure 902.

In some aspects, the enclosure 902 defines a seam 918, formed by portion 902*a* and portion 902*b* being joined together. In some aspects, one or more surfaces of portion 902*a* abut one or more surfaces of portion 902*b*, when the portions 902*a*, 902*b* are coupled together, to form the seam 918. In some aspects, the seam is coplanar with a longitudinal axis of the electrical contact sensor assembly 900. In some embodiments, the seam 918 is includes a separate component, such as a gasket or otherwise seal. In some aspects, the seam 918 (e.g., gasket, seal) is watertight. In some examples, the seam 918 is integral to the enclosure 902.

In some aspects, the enclosure 902 (e.g., portion 902*a*, portion 902*b*) includes one or more enclosure connectors 920. The connectors 920 can include, for example, tabs and/or recesses such that portion 902*a* and portion 902*b* can be coupled together to form the enclosure 902. In some embodiments, portion 902*a* can include connectors 920, such as tabs and recesses, and portion 902*b* can include corresponding connectors 920, such as recesses and tabs. In some aspects, when portion 902*a* and portion 902*b* are coupled together, the seam 918 between the portions 902*a*, 902*b* is watertight.

In one embodiment, the electrical contact sensor assembly 900 includes a flexible PCB assembly 904, a rigid PCB assembly 906, and a single channel for communication between the two. In this manner, the flexible PCB assembly 904 is in communication with the rigid PCB assembly 906. In other embodiments, the electrical contact sensor assembly 900 can include any number of PCBs, which can be any combination of solid, flexible or otherwise, and which can have any number of communication channels between or through them, including but limited to: strips of wire, conductive sheets, and other PCBs.

In one embodiment, the first portion 902a of the enclosure 902 contains all of the electronic components of the electrical contact sensor assembly 900 including, but not limited to, the two circuit boards 904, 906, the contact sensor 930 (e.g., mechanical button), the real time clock and the communication and record-keeping and sending components. The first portion 902a of the enclosure 902 is configured to accommodate each of the internal components of the electrical contact sensor assembly 900 and to inhibit movement of the internal components with respect to the enclosure 902. In other embodiments, the components of the electrical contact sensor assembly 900 can be housed and/or oriented and/or fitted to any number of portions of the enclosure 902, via a single portion (or section) or through collaboration between multiple sections of the enclosure 902, and can prevent movement of any number of the internal components of the electrical contact sensor assembly 900.

In other embodiments, each portion 902a, 902b of the enclosure 902 can cover, in whole or in part, any number of contact sensors 930 and/or sections of the fluid flow path, any number of which may function to protect any of the elements they cover from potential risks to any part of the electrical contact sensor assembly 900, which may include but is not limited to: physical forces, electrical interference, magnetic interference, moisture, acoustics, temperature, bacterial growths, fungal growths, and particulates.

In one embodiment, the enclosure 902 includes two portions (or sections) 902a, 902b that form a watertight seal around the contact sensor 930 and a portion of the IV fluid pathway. In some aspects, the portions 902a, 902b are unitarily constructed such as, for example, permanently connected via a living hinge. In some aspects, the hinge connecting the portions 902a, 902b forms the enclosure 902 as a clamshell. For example, another embodiment of this electrical contact sensor assembly 900 can include a sensor to detect the level of moisture surrounding and/or in contact with the system. In some examples, when the moisture sensor is internal, at least one portion of the enclosure 902 that protects this sensor is configured to allow for moisture to reach the sensor. In some aspects, one portion of the enclosure 902 (e.g., 902a) houses, stores and helps orient both the contact sensor 930 and the medication delivery device (e.g., needleless connector 10) to perform optimally.

In other embodiments, the enclosure 902 can include one or more portion (or sections), any number of which may wholly or in part stabilize and/or contain and/or orient all or part of any of the one or more contact sensors 930 and/or the one or more distinct parts of the fluid flow pathway. Moreover, each of the one or more portions of the enclosure 902 can also function to connect to any other number of the portions of the enclosure 902 and/or sensors and/or sections of the fluid flow path such as by: hooks, friction, hinges, obstruction, adhesives, chemical reactions or sealants. Moreover, any of the one or more portions of the enclosure 902 can be designed to perform any of its intended functions with and/or without connection to any other number of enclosure sections and/or sensors and/or sections of the fluid flow path.

In one embodiment, the enclosure 902 can be constructed of polypropylene. In other embodiments, the enclosure 902 can be constructed of any number of compressible and/or incompressible materials (including but not limited to polycarbonate, PLA, nylon, rubber, bio-glass, glass), any number and combinations of which may be connected in any number of the previously discussed methods. In some aspects, the contact sensor 930, enclosure 902, and medication delivery device (e.g., needleless connector 10) are oriented with each other in a cylindrical shape to minimize the amount of empty space (i.e., occupied by air). In other embodiments, the enclosure 902 can be in any other geometrical shape and configured to optimize of space, minimize empty space, create an optimal ratio of enclosure to sensor(s) to section of IV fluid path, ease of manipulation of the system, and/or co-functionality with any desired device outside of the electrical contact sensor assembly 900.

Figure 14A:
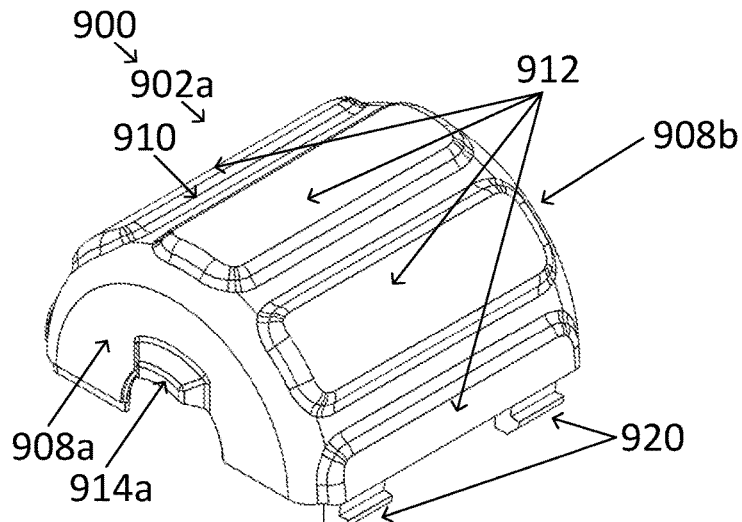
FIGS. 14A-14C illustrate perspective views of the first portion of the enclosure of the example contact sensor assembly.
Figure 14B:
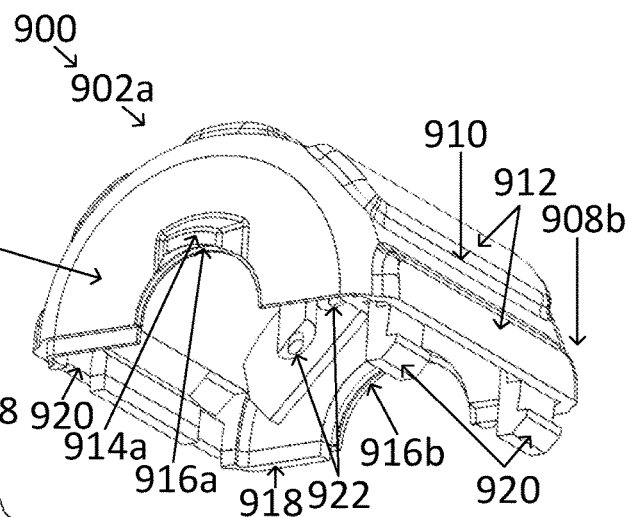
Figure 14C:
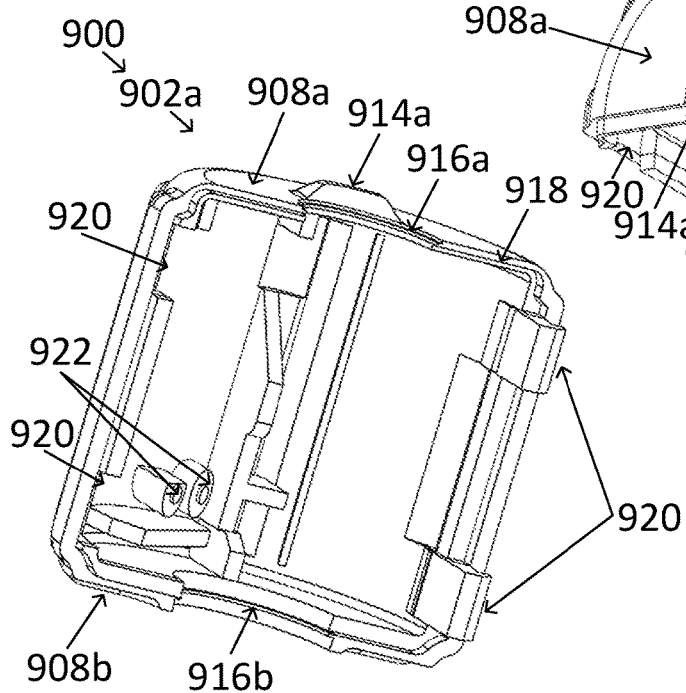
Figure 16A:
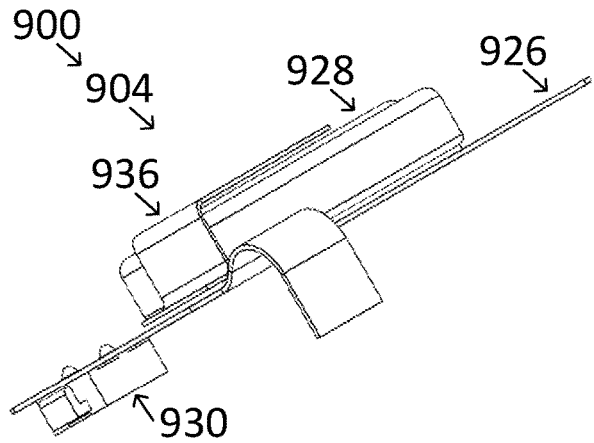
FIGS. 16A-16D illustrate a flexible PCB assembly, which includes a battery and a switch, in a perspective view, perspective view, side view, and perspective view, respectively, according to one embodiment of the present disclosure.
Figure 16B:
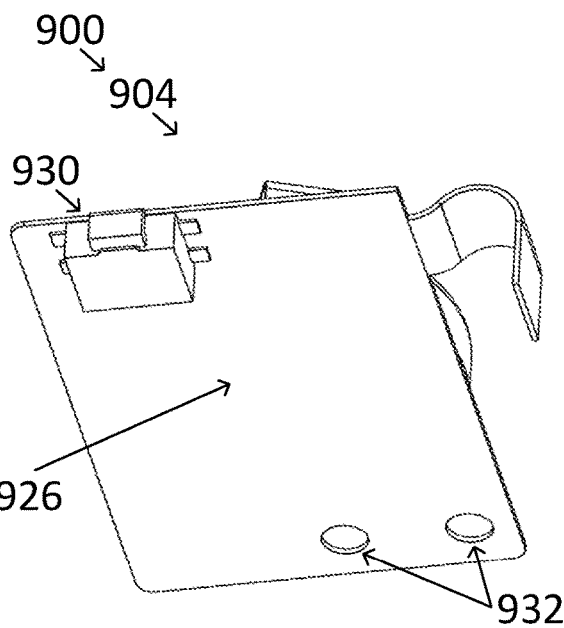
Figure 16C:
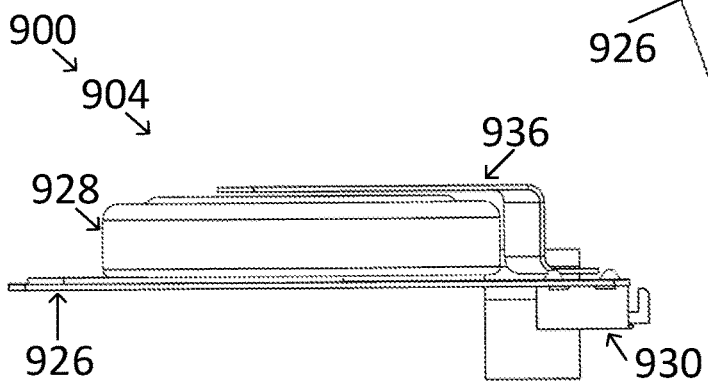
Figure 16D:
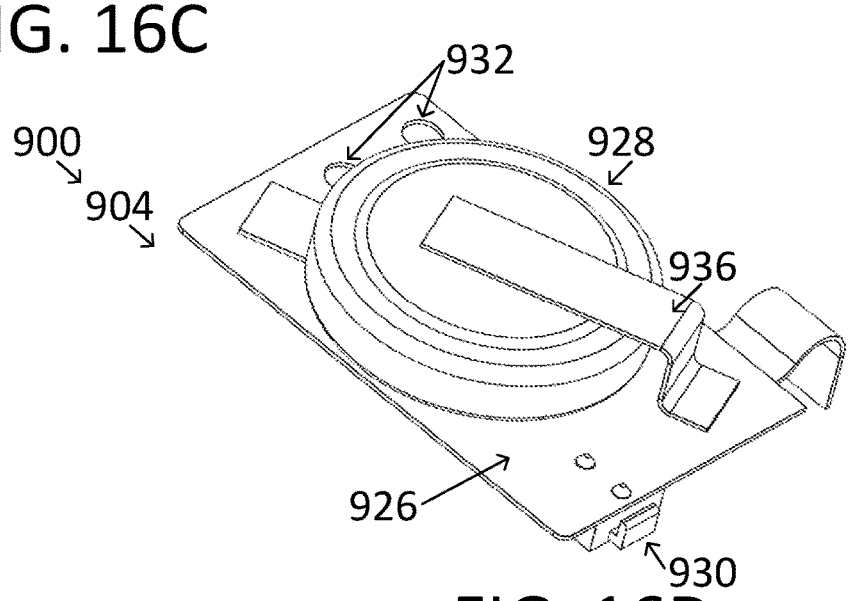

Referring to FIGS. 14A-14C, a first portion 902a of the enclosure 902 of the electrical contact sensor assembly 900 is illustrated in perspective views. As previously discussed, in some examples, the first portion 902a of the of the electrical contact sensor assembly 900 enclosure 902 is part of the housing that contains and protects the sensor and circuits of the electrical contact sensor assembly 900.

The enclosure 902 (e.g., portion 902a) can include one or more internal electronics connectors 922. In some aspects, the electronics connectors 922 defines a surface configured to abut one or more of the internal electronic components (e.g., flexible PCB assembly 904), such as to inhibit movement (e.g., rotation) of one or more of the internal electronic components. In some aspects, the electronics connectors 922 are configured to receive a fastener (e.g., a screw) therein, such as to inhibit movement (e.g., translation) of internal electronic components that receive the fastener therethrough.

The first portion 902a of the enclosure 902 can include a compressible material. The first portion 902a of the enclosure 902 can be constructed of one or more polymers. For example, in one embodiment, the portion 902a can be made of polypropylene. As non-limiting examples, in other embodiments, the first portion 902a can be made of polystyrene, polycarbonate, nylon, and/or rubber.

The portion 902a of the enclosure 902 can include one or more internal rib or ridges (and associated grooves) to orient, support, and maintain the position of the medication delivery device (e.g., needleless connector 10) within the electrical contact sensor assembly 900. For example, the ribbing can be configured to be complementary to the exterior surfaces of the needleless connector 10 to orient, support, and maintain the position of the needleless connector 10.

The first end 908a of the enclosure 902 can include one or more extrusions 914 (e.g., 914a) extending from the first end 908a. The extrusions 914 can define an outer surface that is configured may be the point of contact for a connecting device, such as the pump connector 18, when the connector is connected to the medication delivery device (e.g., needleless connector 10). A distance measured between the first end 908a of the enclosure 902 and the outer surface of the extrusion 914 can be configured to decrease the amount of force required to rotate the connector and/or medication delivery device (e.g., needleless connector 10) to fluidly couple the connector to the medication delivery device. Lips can be incorporated on the interior ring (e.g., at the interface between the needleless connector 10 and the enclosure 902) to create a seal with the needleless connector 10 to form a water-tight seal and prevent fluid from penetrating into the electrical contact sensor assembly 900.

In one embodiment, the first portion 902a of the enclosure 902 includes connectors 920 (also referred to as points of connection) to connect the first portion 902a of the enclosure 902 to the second portion 902b of the enclosure 904, thereby enclosing the enclosure 902 around the medication delivery device (e.g., needleless connector 10) and the internal components of the electrical contact sensor assembly 900. In one embodiment, the connectors 920 include a combination of snap fit tabs and tab receivers. In other embodiments, the connectors 920 can include hooks, a dynamic seal, friction, physical obstruction, a living hinge, sealant, or any other mechanical or chemical adherence mechanism. Furthermore, in other embodiments, each section of the enclosure 902, via connection with any other number of enclosures 902 or by itself, serve to function as a watertight or antibacterial seal (i.e., barrier) for any number or portions of sensor components/and/or sections of the medication flow path.

When the enclosure 902 is assembled (e.g., when the first portion 902a is coupled to the second portion 902b), the enclosure 902 can form a generally cylindrical shape having a generally curved surface (e.g., shell 910) and two bases (e.g., first end 908a, second end 908b). In other examples, the shape of the enclosure 902 can be conical, rectangular, or any other reasonably regular shape. The exterior cylindrical surface can include surface features 912 (e.g., ridges) that are configured to improve the grip and torque when connecting the electrical contact sensor assembly 900 and/or when connecting the fluid flow path. The bases can include a thin, compressible wall to allow for motion that translates motion to the internal contact sensor 930.

Referring to FIGS. 15A-15C, a second portion 902b of the enclosure 904 of the electrical contact sensor assembly 900 is illustrated in perspective views. The second portion 902b of the enclosure 902 is part of the housing that contains and protects the sensor and circuits.

The second portion 902b of the enclosure 904 can be constructed of a compressible material. The second portion 902b can be made of one or more polymers. For example, in one embodiment, the second portion 902b can be made of polypropylene. As non-limiting examples, in other embodiments, the second portion 902b can be made of polystyrene, polycarbonate, nylon, and/or rubber.

The second portion 902b of the enclosure 904 can include a one or more internal structures 924 (e.g., ribs or ridges and associated grooves) that orient, support, and maintain the position of the medication delivery device (e.g., needleless connector 10) within the electrical contact sensor assembly 900. In some aspects, the internal structures 924 are configured to be complementary to the outer surfaces 16 of the needleless connector 10 to orient, support, and maintain the position of the needleless connector 10. In some aspects, the internal structures 924 abut the outer surface 16 of the medication delivery device (e.g., needleless connector 10) to inhibit movement (e.g., translation, rotation) of the medication delivery device with respect to the enclosure 902 of the electrical contact sensor assembly 900.

The first end 908a of the enclosure 902 can include an extrusion 914 (e.g., 914a) extending therefrom. The extrusion 914 can define an outer surface that is configured to be the point of contact for a connector, such as the pump connector 18, when the connector is connected to the medication delivery device (e.g., needleless connector 10). A distance measured between the first end 908a of the enclosure 902 and the outer surface of the extrusion 914 can be configured to decrease the amount of force required to rotate the connector and/or medication delivery device (e.g., needleless connector 10). Lips can be incorporated on the interior ring (e.g., at the interface between the needleless connector 10 and the enclosure 902) to create a seal with the needleless connector 10 to form a water-tight seal and prevent fluid from penetrating into the electrical contact sensor assembly 900.

In one embodiment, the second portion 902b of the enclosure 902 includes connectors 920 (also referred to as points of connection) to connect the second portion 902b of the enclosure 902 to the first portion 902a of the enclosure 902, thereby enclosing the enclosure 902 around the medication delivery device (e.g., needleless connector 10) and the internal components of the electrical contact sensor assembly 900. In one embodiment, the connectors 920 include a combination of snap fit tabs and tab receivers. In other embodiments, the connectors 920 can include hooks, a dynamic seal, friction, physical obstruction, a living hinge, sealant, or any other mechanical or chemical adherence mechanism. Furthermore, in other embodiments, each section of the enclosure 902 may, via connection with any other number of enclosures 902 or by itself, serve to function as a watertight or antibacterial seal (i.e., barrier) for any number or portions of sensor components/and/or sections of the medication flow path.

When the enclosure 902 is assembled (e.g., when the first portion 902a of the enclosure 902 is coupled to the second portion 902b of the enclosure 902), the enclosure 902 can form a generally cylindrical shape having a generally curved surface (e.g., shell 910) and two bases (e.g., first end 908a, second end 908b). The exterior cylindrical surface can include surface features 912 (e.g., ridges) that are configured to improve the grip and torque when connecting the electrical contact sensor assembly 900 and/or when connecting the fluid flow path. The bases can include a thin, compressible wall to allow for motion that translates motion to the internal contact sensor 930.

In one embodiment, the interior of the second portion 902b of the enclosure 902 is configured to maintain, support, or lock the needless connector 10 into a preferred position by being specially designed to fit the physical features of the needleless connector 10 and to prevent movement of the needleless connector 10 once it is received within the enclosure 902. In some examples, multiple tabs, supports notches, and ridges prevent motion in one or more dimensions. In other embodiments, the second half of the enclosure may be configured to lock and/or orient any number or portions of sensors and any number of sections of the IV fluid pathway into their preferred locations.

The internal structures 924 can be configured to be physical complimentary to the shape of the medication delivery device (e.g., needleless connector 10) in order to minimize both the amount of unused space and the opportunity for movement of the needless connector in any direction. In other embodiments, the aforementioned features can stabilize and/or orient and/or limit a needleless connector 10 or other section(s) of the IV fluid pathway that can be monitored by one or more electrical contact sensor assemblies 900. In other embodiments, the aforementioned features can also stabilize and/or orient any number of components of the device, including but not limited to the PCBs 904, 906, the contact sensor 930, and the battery 928.

Referring to FIGS. 16A-16D, a flexible PCB assembly 904 of the electrical contact sensor assembly 900 is illustrated in a perspective view, perspective view, side view, and perspective view, respectively, according to one embodiment of the present disclosure. In some aspects, the flexible PCB assembly 904 includes a flexible PCB 926 that contains a battery 928 and a contact sensor 930 (also referred to as a contact switch or electrical contact switch). The flexible PCB assembly 904 may also include an electrical connection to connect the switch and battery to the rigid PCB assembly 906. The battery may be operable to power the microcontroller, BLE antenna, resistors, a real time clock, and other components. In other embodiments, any number of other components of the electrical contact sensor assembly 900 can be located on the flexible PCB assembly 904. The switch may be configured to be in communication with the sidewalls of the enclosure so that the switch compresses when a fluid flow path is connected and the sidewalls compress.

In one embodiment, the battery 928 and contact sensor 930 are located on opposite sides of the flexible PCB 926. For example, the battery 928 can be located on the radially outward facing surface of the flexible PCB 926 and the contact sensor 930 can be located on the radially inward facing surface of the flexible PCB 926. In other examples, the battery 928 and contact sensor 930 can be located on the same side of the flexible PCB 926, either on the radially outward facing surface or the radially inward facing surface. In other embodiments, the battery 928 and/or the contact sensor 930 can be located on a rigid PCB. In other embodiments, the battery 928 and contact sensor 930 can be distributed amongst several PCBs.

Figure 17A:
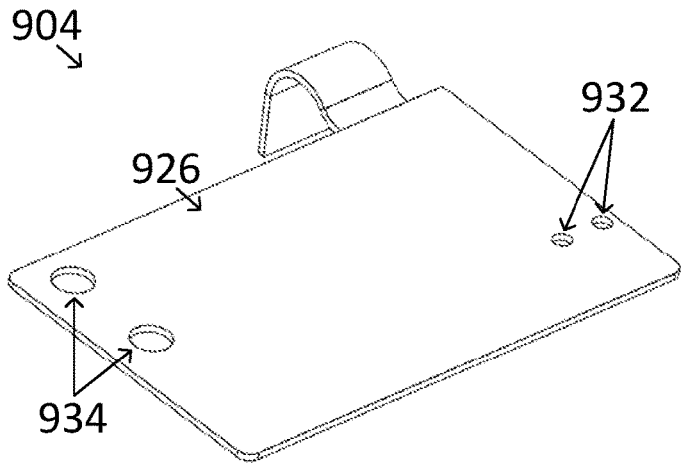
FIGS. 17A-17C illustrate the flexible PCB in a perspective view, top view, and perspective view, respectively, according to one embodiment of the present disclosure.
Figure 17B:
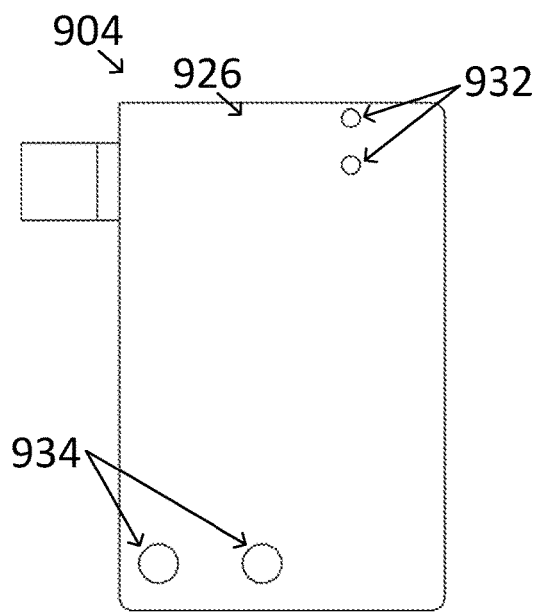
Figure 17C:
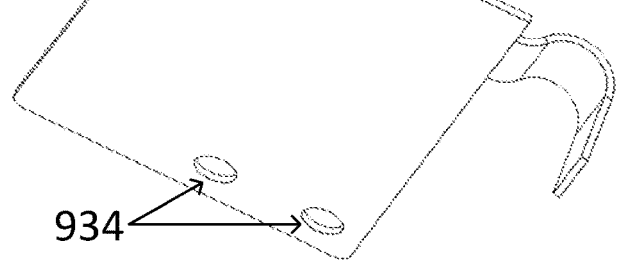
Figure 19A:
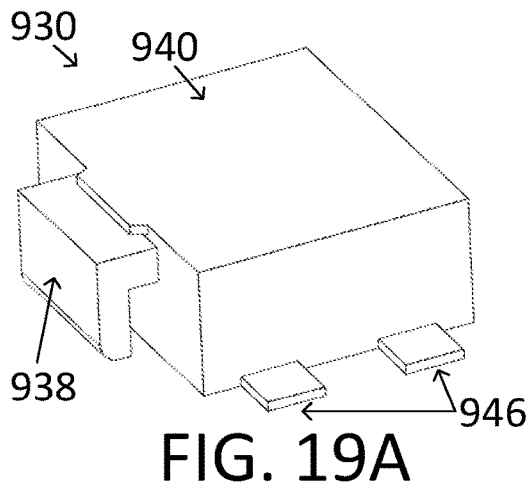
FIGS. 19A-19E illustrate a contact sensor in a perspective view, perspective view, front view, side view, and bottom view, respectively, according to one embodiment of the present disclosure.
Figure 19B:
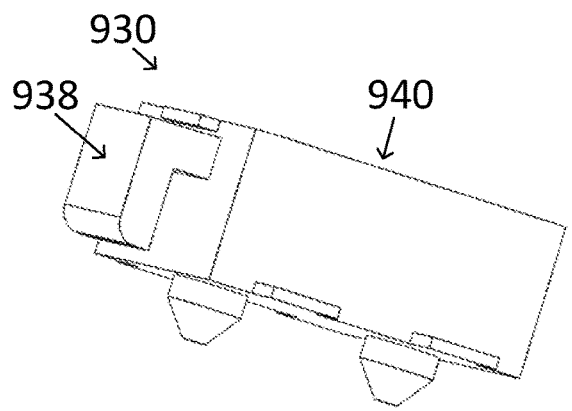
Figure 19C:
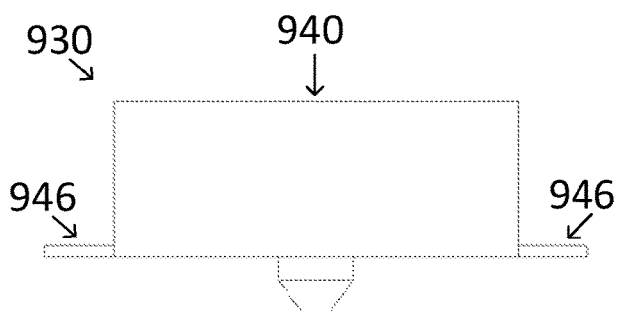
Figure 19D:
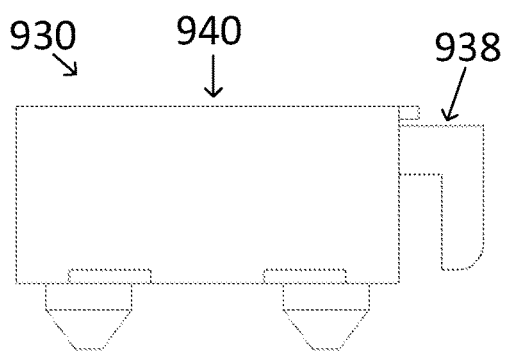
Figure 19E:
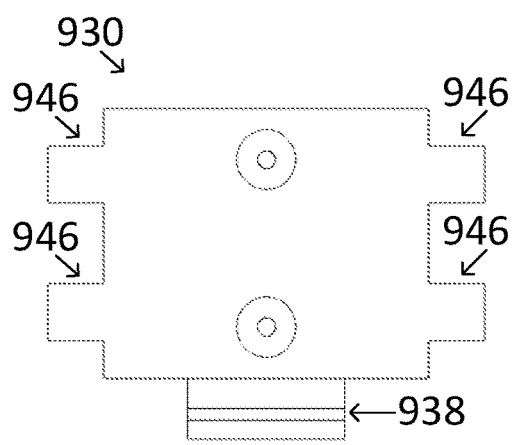

Referring to FIGS. 17A-17C, a flexible PCB 926 is illustrated in a perspective view, top view, and perspective view, respectively, according to one embodiment of the present disclosure. The flexible PCB 926 can include a battery 928 and a contact sensor 930 (as illustrated for example in the flexible PCB assembly 904 in FIGS. 16A-16D). The flexible PCB 926 can include electrical connections points 932 (as illustrated in FIGS. 17A-17D), which can be used to electrically couple the contact sensor 930 to the flexible PCB 926. The flexible PCB 926 can include apertures 934, which can be used to couple (e.g., removably couple) the flexible PCB 926 to the enclosure 902 (e.g., portion 902a). For example, as illustrated in FIG. 13B, the apertures 934 of the flexible PCB 926 can be aligned with the electronics connectors 922 of the enclosure 902 (e.g., portion 902a). In this manner, a fastener (e.g., screw) can be inserted through the apertures 934 of the flexible PCB 926 and advanced into the electronics connectors 922 of the enclosure 902 to couple (e.g., removably couple) the flexible PCB 926 to the enclosure 902.

Referring to FIGS. 18A-18C, a battery 928 is illustrated in a perspective view, side view, and bottom view, respectively, according to one embodiment of the present disclosure. The battery 928 can be mounted to the flexible PCB 926 (as illustrated for example in FIGS. 16A-16D), on a ridged PCB, or on another form of platform. In some aspects, a battery contact 936 (e.g., leaf spring) can extend from the flexible PCB 926 (as illustrated for example in FIGS. 16A-16D). The battery contact 936 can receive the battery 928 therein such that the battery 928 is in electrical communication with the flexible PCB 926. When connected to the flexible PCB 926 (e.g., connected to battery contact 936), the battery 928 can discharge such that current flows through the circuit. Current flow through the circuit can depend upon the position of the actuator 938 of the contact sensor 930, as discussed below.

Figure 20:
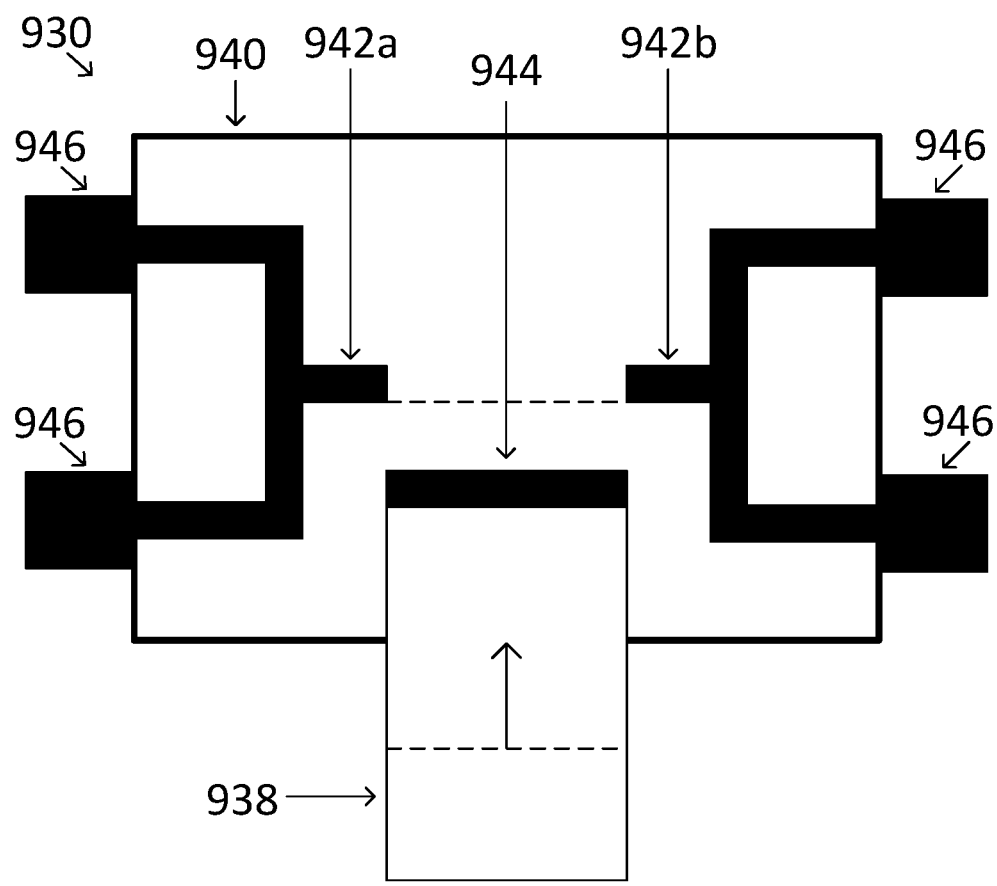
FIG. 20 illustrates the internal components of a contact sensor in a top view, according to one embodiment of the present disclosure.

Referring to FIGS. 19A-E, a contact sensor 930 is illustrated in a perspective view, perspective view, front view, side view, and bottom view, respectively, according to one embodiment of the present disclosure. A cross-sectional view of the internal components of the contact sensor 930 is illustrated in FIG. 20, according to one embodiment of the present disclosure. The contact sensor 930 is configured to monitor a state of electrical connection (e.g., electrically connected, not electrically connected). In some embodiments, the contact sensor 930 is disposed within the enclosure 902. For example, the contact sensor 930 can be mounted to the flexible PCB 926 (as illustrated for example in FIGS. 16A-16D).

The contact sensor 930 (also referred to as a switch) includes an actuator 938. The actuator 938 can be, for example, a push button actuator, a plunger actuator, a slide actuator, a toggle actuator, a rotary actuator, a pull actuator, or a combination thereof. In some aspects, the actuator 938 is biased (e.g., biased outward) by a compressible mechanism and/or may be integrated with the compressible mechanism. The compressible mechanism can be, for example, a spring, button, elastic elastomeric material, piezoelectric device, or any material with an elastomeric constant or spring constant, or a combination thereof. In one embodiment, the contact sensor 930 includes a push button actuator that is biased by the elastic wall of the enclosure 902 of the electrical contact sensor assembly 900. In another embodiment, the contact sensor 930 can include a material that changes condition in response to pressure, that is biased by a one or more actuator that supplies this pressure.

In some aspects, the actuator 938 of the contact sensor 930 is in communication with the enclosure 902 (e.g., first end 908a), as illustrated for example in FIGS. 13A-13B. Movement or otherwise deflection of the enclosure 902 causes corresponding movement of the actuator 938. In some examples, compression of the first end 908a of the enclosure 902 causes corresponding depression of the actuator 938 and relaxation (or rebound) of the first end 908a causes extension of the actuator 938. In this manner, the state of electrical (e.g., electrically connected, not electrically connected) of the contact sensor 930 can correspond to the position of the enclosure 902 (e.g., first end 908a).

The contact sensor 930 can include an exterior housing 940, electrical contacts 942 (e.g., 942a, 942b), and/or an actuator 938 operable to electrically connect the electrical contacts 942. The bottom of the exterior housing 940 can contain conductive tabs 946 that connect with the circuit. The actuator 938 can be integrated into the housing 940 of the contact sensor 930 and operable to actuate (e.g., depress, rebound) with respect to the housing 940. The actuator 938 can include a first end that is located within the housing 940 of the contact sensor 930 and a second end that is located outside of the housing 940, wherein the actuator 938 extends outwardly from the housing 940.

In one embodiment, the second end of the actuator 938, which is outside of the housing 940 of the contact sensor 930, is in mechanical communication with the enclosure 902 of the electrical contact sensor assembly 900. As a result, the contact sensor 930 is configured so that the actuator 938 is depressed (i.e., actuated) (acts like a spring) when the enclosure 902 of the electrical contact sensor assembly 900 is compressed. In other words, compressive force applied to at least a section of the enclosure 902 (e.g., the compressible first end 908a) of the electrical contact sensor assembly 900 is translated into compressive/translational force applied to the actuator 938 of the contact sensor 930. In some aspects, the enclosure 902 (e.g., first end 908a) of the electrical contact sensor assembly 900, which functions as the compressible mechanism, is operable to bias the first and second electrical contacts 942a, 942b from establishing an electrical connection.

The actuator 938 can actuate (e.g., depress) inwardly with respect to the housing 940 of the contact sensor 930 when force (e.g., compressive force) is applied to the actuator 938 (e.g., push button actuator) such as when the first end 908a of the enclosure 902 compresses inward (e.g., when a connector, such as a pump connector, is connected to the medication delivery device (e.g., needleless connector 10). The compressible mechanism (e.g., spring) can cause the actuator 938 to return to an undepressed position when the compressive force is removed. In other words, the actuator 938 is in a first position (e.g., undepressed) when no compressive force or insufficient force is applied. Then, the actuator 938 is actuated (e.g., depressed) when sufficient compressive force is applied, whereby the actuator 938 moves into a second position (e.g., depressed). Then, as a result of the compressible mechanism that biases the actuator 938 with respect to the contact sensor 930, the actuator 938 moves back to the first position (e.g., undepressed) when the force is removed.

In one embodiment, as illustrated for example in FIG. 20, the contact sensor 930 contains two electrical contacts on opposite sides of the contact sensor 930. The first electrical contact 942a is separated from the second electrical contact 942b on the opposite side of the switch. The first end of the actuator 938, which is located within the housing 940 of the contact sensor 930, contains an electrically conductive element 944 that is configured to connect the first electrical contact 942a and the second electrical contact 942b when the actuator 938 is actuated (e.g., depressed). In one embodiment, the conductive element 944 at the first end of the actuator 938 is ferrous metal. In other embodiments, the conductive element 944 can be a conductive metal or conductive polymer. In other embodiments, the contact sensor 930 can include less than two electrical contacts 942 or more than two electrical contacts 942. Moreover, the contact sensor 930 can include less than four conductive tabs 946 or more than four conductive tabs 946.

In some embodiments, when a sufficient force is applied to the actuator 938, the actuator 938 actuates (e.g., depresses) and completes an electrical circuit within the contact sensor 930. The completion of the electrical circuit sends an electrical signal as a change in state of the electrical connection (e.g., electrically connected, not electrically connected). As previously discussed, the state of the electrical connection corresponds to the state of connection of the medication delivery device (e.g., connected, not connected), which can correspond to the state of fluid flow through the medication delivery device (which can be part of an IV fluid flow pathway). When a force is no longer applied to the actuator 938, the actuator 938 returns to its original position (e.g., via the compressible mechanism such as a spring), which is an open circuit. In other embodiments, the contact sensor 930 can contain one or more distinct circuits, any number and/or states of which may represent the original/resting position. In other embodiments, the signaling can be the opposite, such that presence of electrical connection indicates a disconnection of the medication delivery device, and a disconnection indicates a connection of the medication delivery device.

The contact sensor 930 can be configured as either a normally open switch or a normally closed switch. In one embodiment, in the normally open configuration, the circuit is not complete (i.e., open) when no compressive force is applied to the actuator 938. Then, when compressive force is applied to the actuator 938, the actuator 938 actuates (e.g., depresses) and the circuit is completed (i.e., closed). The removal or release of compressive force causes the actuator 938 to return to its original position and the circuit is not complete (i.e., open). In another embodiment, in the normally closed configuration, the circuit is complete (i.e., closed) when no compressive force is applied to the actuator 938. Then, when compressive force is applied to the actuator 938, the actuator 938 actuates (e.g., depresses) and the circuit not complete (i.e., open). The removal or release of compressive force causes the actuator 938 to return to its original position and the circuit is complete (i.e., closed).

In one embodiment, the contact sensor 930 can be mounted to the flexible PCB 926 of the flexible PCB assembly 904. The contact sensor 930 can contain electrical tabs 946 that electrically connect the contact sensor 930 to the flexible PCB 926 (e.g., the flexible PCB assembly 904) and, correspondingly, to the other circuit components of the electrical contact sensor assembly 900. In other embodiments, the contact sensor 930 can be mounted to the rigid PCB 948 of the rigid PCB assembly 906 and configured to be used in a similar manner as previously described.

In one embodiment, the force applied to actuate (e.g., depress) the actuator 938 is an applied compressive force. A change of state occurs when the push button actuator is actuated (e.g., depressed from an undepressed position). In other embodiments, the applied force can be frictional force, tension force, normal force, applied force, spring force, frictional force, gravitational force, magnetic force translational force, or a combination thereof.

In other embodiments, one or more actuating components can be incorporated for one or more forces of any combination and type(s) to bias in one or more directions for each compressible component(s), each of which may cause the change of state of the same or unique one or more electrical pathways, each of which may then be interpreted as one or more changes in one or more states of the one or more sections of the IV fluid pathway. As non-limiting examples, these actuating components may include: a compressible conductive material, a spring, an elastic material, a fluid-filled container, or any other component and/or system with a reasonably consistent spring constant.

Figure 21A:
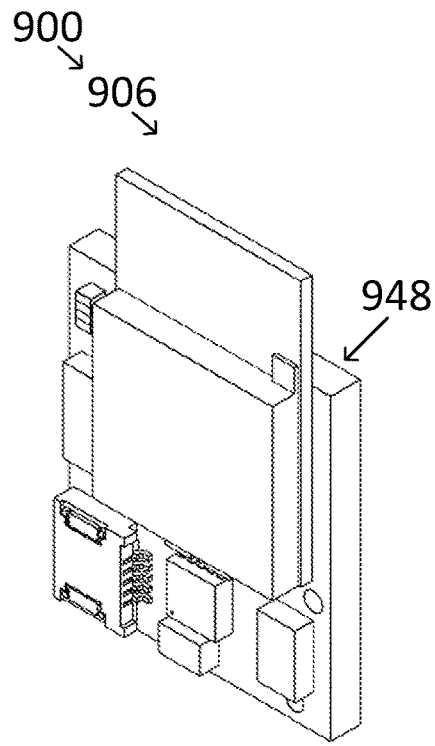
FIGS. 21A-21C illustrate a rigid PCB assembly, which includes a microcontroller and BLE antenna, in a perspective view, front view, and perspective view, respectively, according to one embodiment of the present disclosure.
Figure 21B:
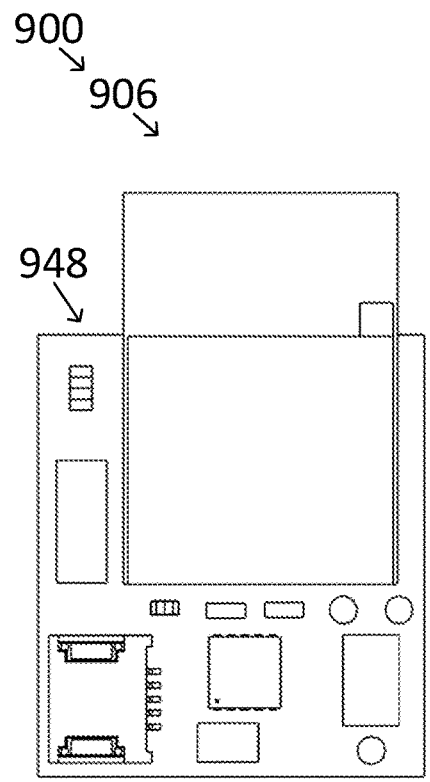
Figure 21C:
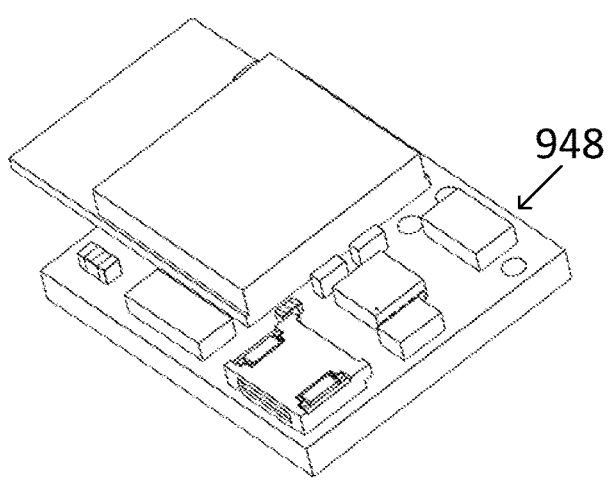

Referring to FIGS. 21A-21C, a rigid PCB assembly 906 of the electrical contact sensor assembly 900 is illustrated in a perspective view, front view, and perspective view, respectively. The rigid PCB assembly 906 can include a rigid PCB 948 that includes a microcontroller, BLE antenna, resistors, a real time clock, and other components. The microcontroller and BLE antenna can be configured to record when the circuit is connected and/or disconnected. Moreover, the microcontroller and BLE antenna can be configured to share, send, or otherwise communicate this data to a separate device. The real time clock can be configured to provide a timestamp associated with the connection and/or disconnection of the circuit.

In one embodiment, the microcontroller, BLE antenna, resistors, real time clock, and all other components can be located on a single side of a rigid PCB 948. For example, the components can all be located on the radially outward facing surface of the rigid PCB 948. In other examples, the components can be located on a combination of the radially inward facing surface and radially outward facing surface of the rigid PCB 948 or the components can all be located on the radially inward facing surface of the rigid PCB 948. In other embodiments, the components can be located on a flexible PCB. In other embodiments, the components can be distributed amongst several PCBs. In other embodiments, the components can be on a hybrid PCB.

In some aspects, the controller can relay feedback to an authorized user (e.g., nurse, doctor, healthcare provider, patient). In some aspects, the feedback can include the time of day, duration of infusion, schedule of infusion, whether or not a cap was connected to the medication delivery device, and/or whether the correct procedure was followed. In other aspects, the feedback can include whether or not data related to the infusion (e.g., change of state of the contact sensor) was relayed by the controller and/or whether or not the data related to the infusion matches a therapy regimen (e.g., treatment plan).

Figure 22A:
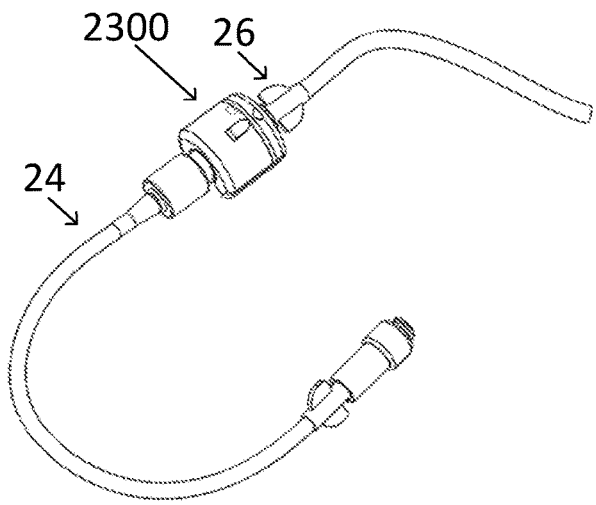
FIGS. 22A-22C illustrate an electrical contact sensor assembly attached to an extension set, according to one embodiment of the present disclosure.
Figure 22B:
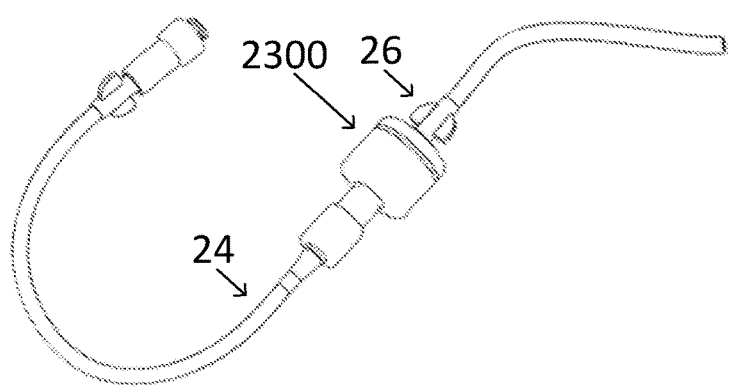
Figure 22C:
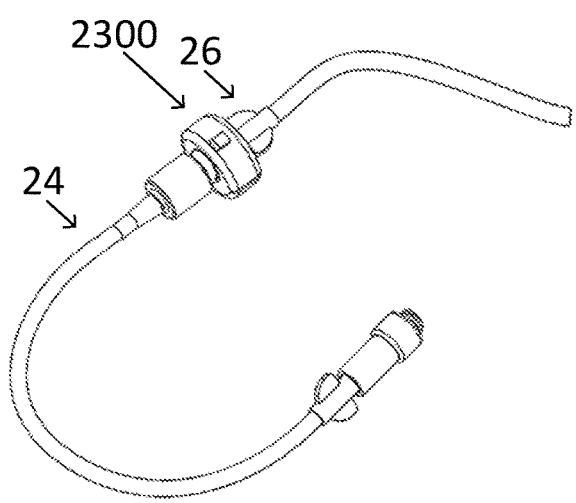

Referring to FIGS. 22A-22C, an electrical contact sensor assembly 2300 is illustrated, according to one embodiment of the present disclosure. The electrical contact sensor assembly 2300 is illustrated in detail in FIGS. 23A-23B. The electrical contact sensor assembly 2300, as illustrated in FIGS. 22A-22C, is attached to an extension set 24, which can be fluidly coupled to a broader fluid flow path. For example, the extension set 24 (e.g., the male end of the extension set 24) can be coupled to a female fitting 26, as illustrated for example in FIGS. 22A-22C. It should be noted that although FIGS. 22A-22C illustrate the electrical contact sensor assembly 2300 attached to an extension set 24, the electrical contact sensor assembly 2300 disclosed herein is not limited to use with an extension set 24. For example, the electrical contact sensor assembly 2300 can be configured to attach to any medication delivery device having a luer lock end, which includes but is not limited to a needleless connector 10 (as illustrated for example in FIGS. 23A-23B), an extension set 24 (as illustrated for example in FIGS. 23A-23C, an end of an IV-line implant, an end of a medication source. It should be noted that FIG. 22C illustrates an electrical contact sensor assembly 2300 that is shorter along the longitudinal axis that the electrical contact sensor assemblies 2300 illustrated in FIGS. 22A-22B.

Figure 23A:
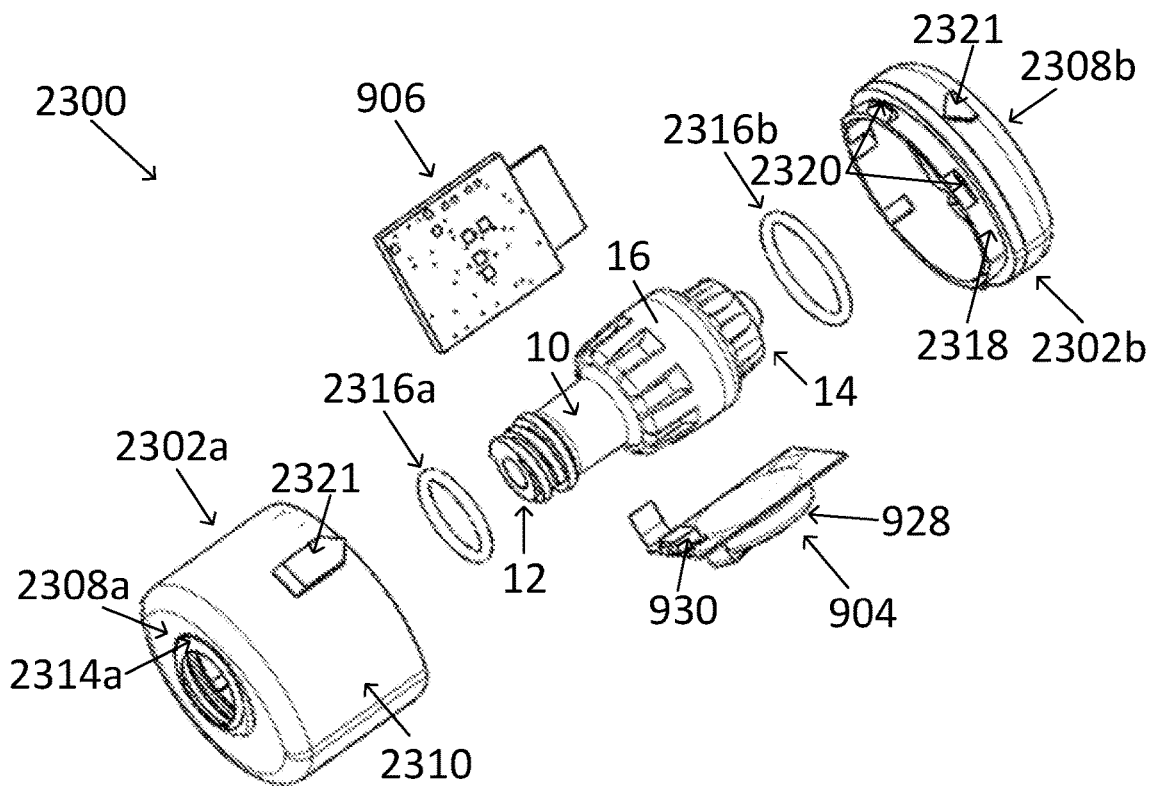
FIGS. 23A-23B illustrate an electrical contact sensor in an exploded, perspective view and in an exploded, perspective view, according to one embodiment of the present disclosure.
Figure 23B:
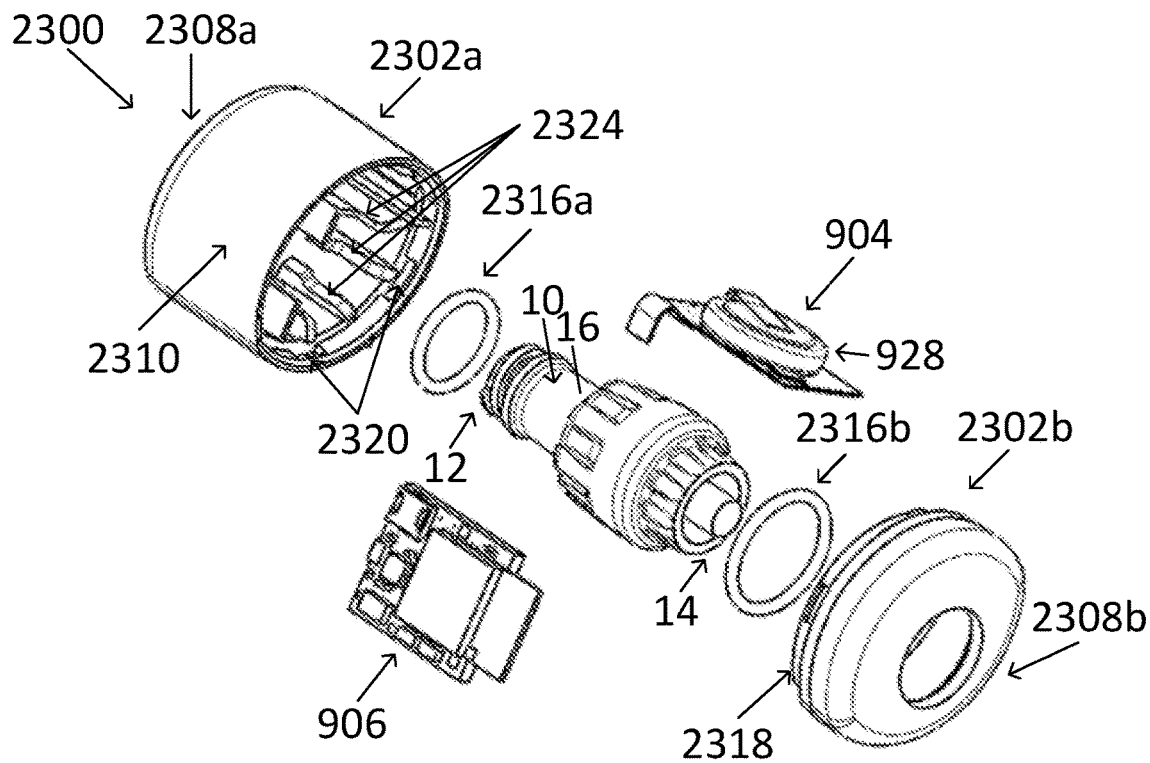
Figure 24A:
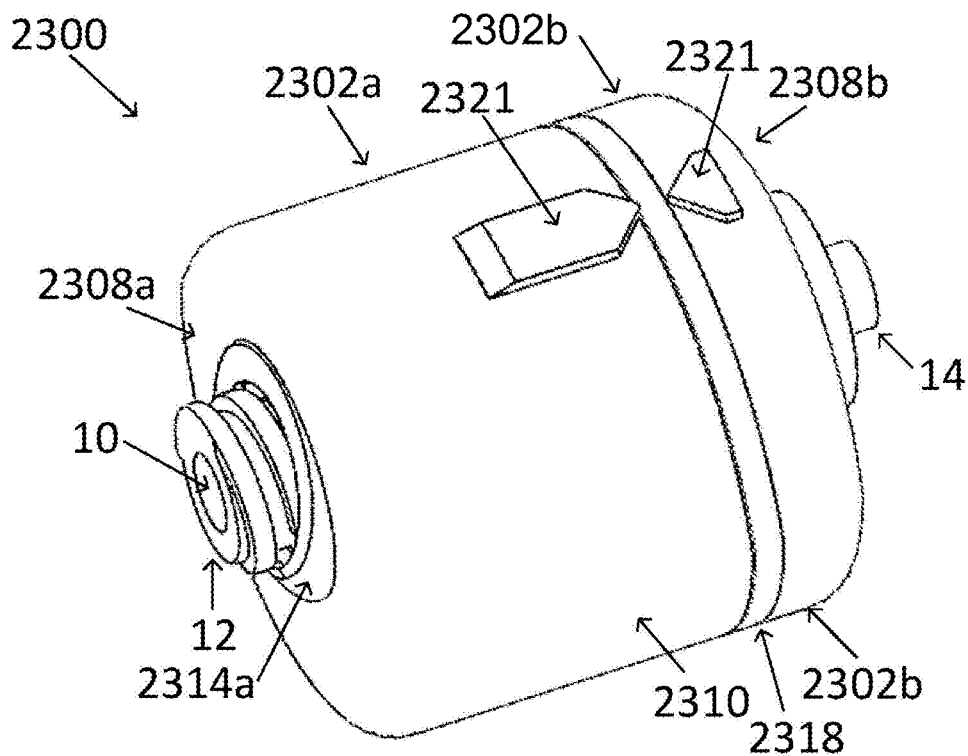
FIGS. 24A-24E illustrate an electrical contact sensor in a perspective view, perspective view, top view, side view, and side view, respectively, according to one embodiment of the present disclosure.
Figure 24B:
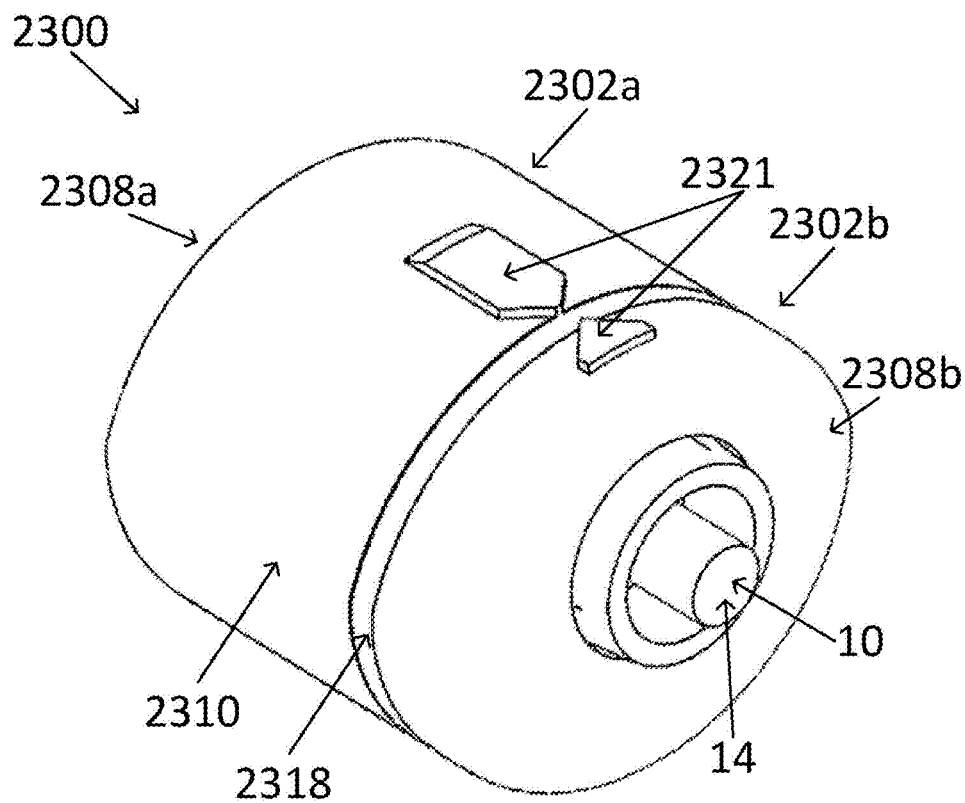
Figure 24C:
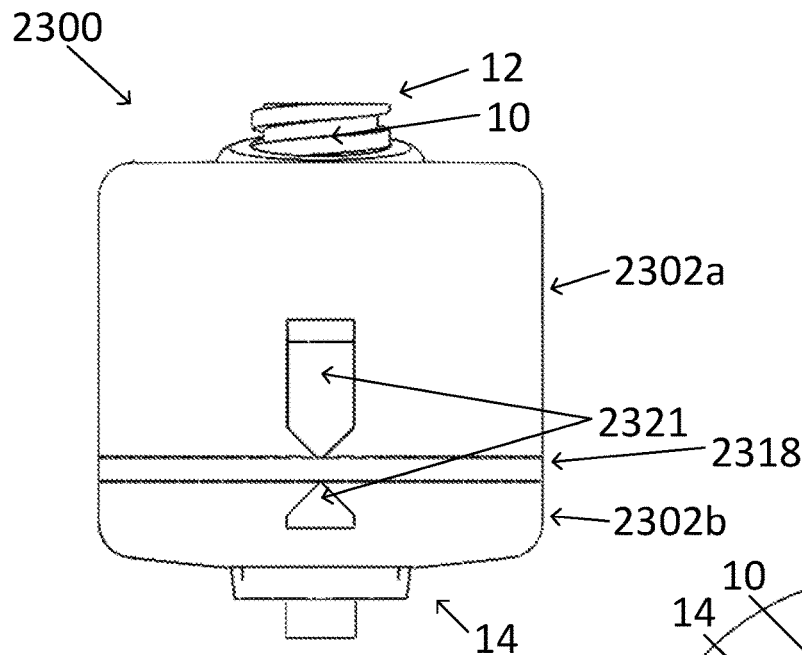
Figure 24D:
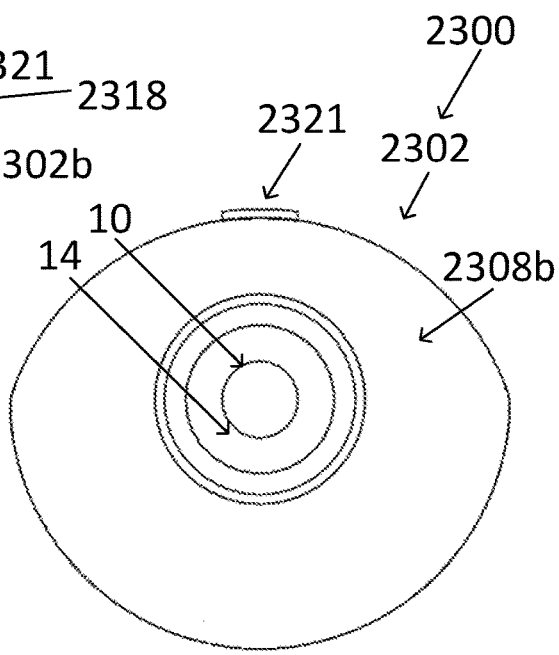
Figure 24E:
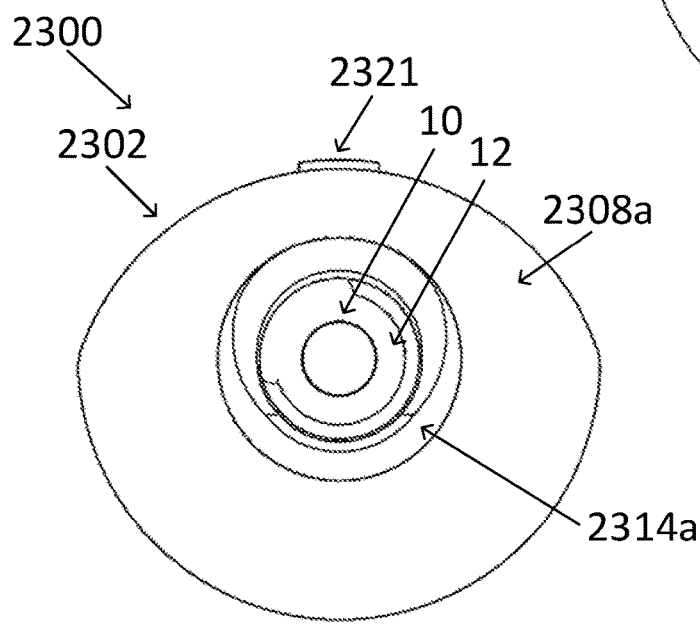
Figure 25A:
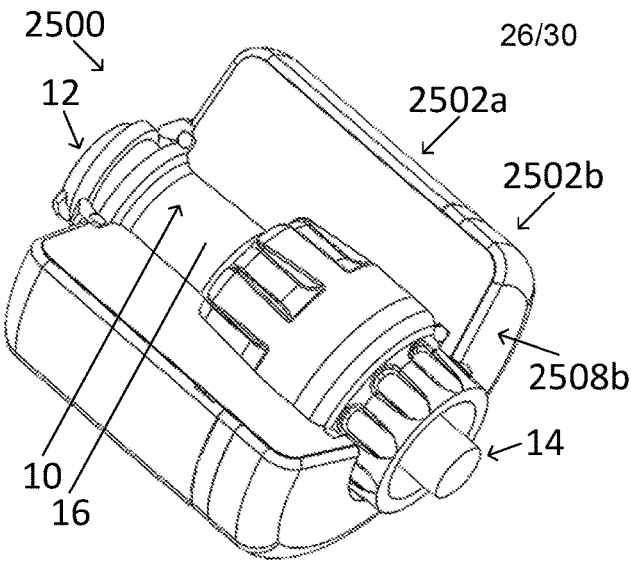
FIGS. 25A-25D illustrate a contact sensor assembly in a perspective view, side view, perspective view, and side view, respectively, according to one embodiment of the present disclosure.
Figure 25B:
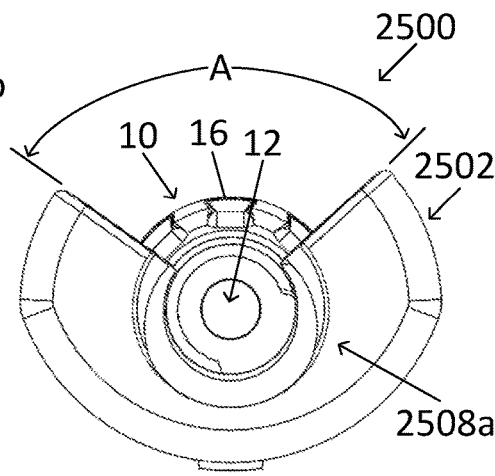
Figure 25C:
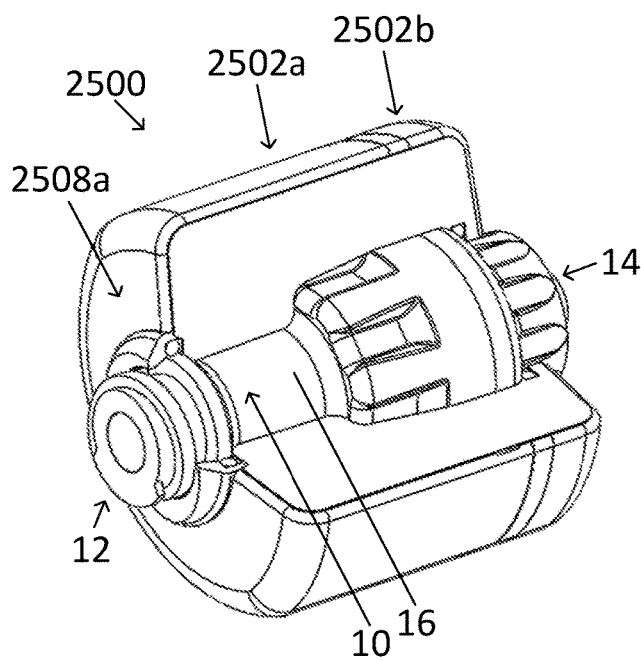
Figure 25D:
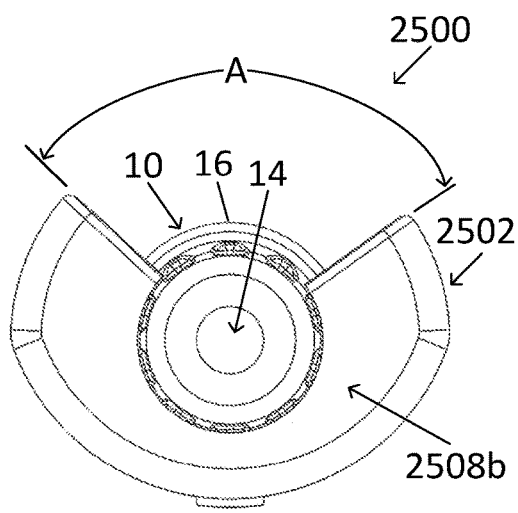
Figure 26A:
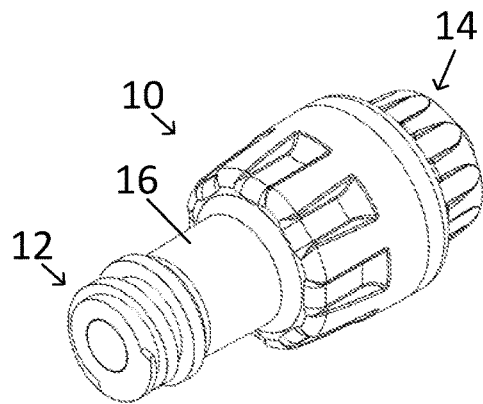
FIGS. 26A-26D illustrate a needleless connector in a perspective view, perspective view, top view, and side view, respectively.
Figure 26B:
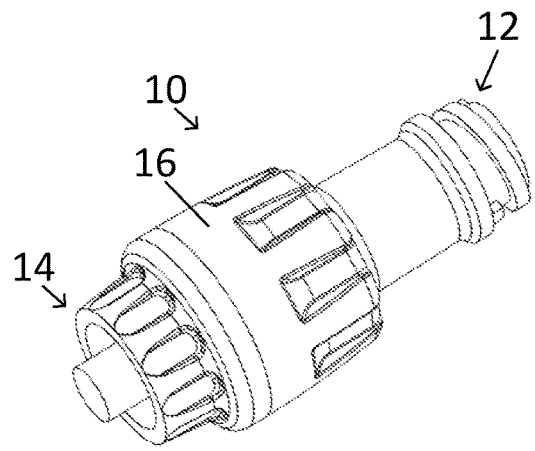
Figure 26C:
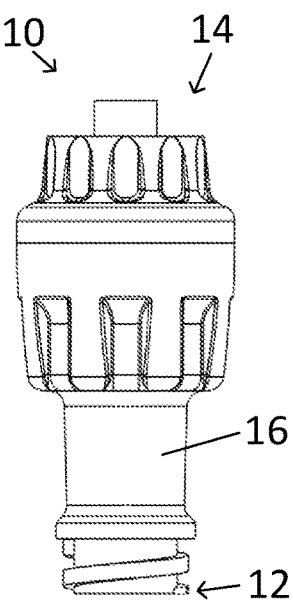
Figure 26D:
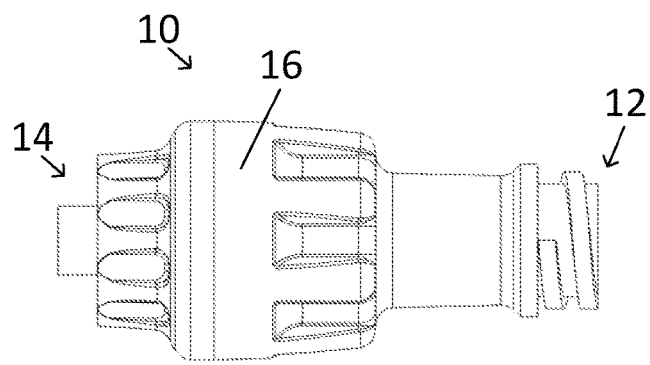

Referring now to FIGS. 23A-23B, one aspect of an electrical contact sensor assembly 2300 is illustrated, in a perspective, exploded view and a perspective, exploded view, respectively. The electrical contact sensor assembly 2300 (as illustrated for example in FIGS. 23A-23B) can have one or more same or similar features as the electrical contact sensor assembly 900 (as illustrated for example in FIGS. 9-10). Due to the same or similar features, the reference numbers and corresponding description provided above for various components, elements, portions, etc., of the electrical contact sensor assembly 900 in FIGS. 9-10 can be generally applied to the same or similar components, elements, portions, etc., provided for the electrical contact sensor assembly 2300 in FIGS. 23A-23B; however, the reference numbers in FIGS. 23A-23B are 2300 series rather than 900 series. In one embodiment, the electrical contact sensor assembly 2300 includes an enclosure 2302 (e.g., 2302a, 2302b) with internal components such as, for example, a flexible PCB assembly 904 and/or a rigid PCB assembly 906.

In some embodiments, the enclosure 2302 (e.g., 2302a, 2302b) includes portion 2302a and portion 2302b, which are configured to couple (e.g., snap) together to form the enclosure 2302. The enclosure 2302 has a first end 2308a and a second end 2308b opposite the first end 2308a and a shell 2310. In some aspects, the enclosure 2302 is generally cylindrical in shape, such that the first end 2308a is a first base, the second end 2308b is a second base, and the shell 2310 defines a generally curvate surface. In some aspects, the first end 2308a and/or the second end 2308b define a generally planar surface that, when the enclosure 2302 is attached to the medication delivery device (e.g., needleless connector 10), the first end 2308a and/or the second end 2308b are generally perpendicular to a longitudinal axis of the medication delivery device. In some aspects, the shell 2310 defines a surface that, when the enclosure 2302 is attached to the medication delivery device, the shell 2310 is generally parallel to the longitudinal axis of the medication delivery device.

The enclosure 2302 can include one or more extrusions 2314 (e.g., 2314a), which can be a first point of contact to induce mechanical compression of the enclosure 2302. In some aspects, the extrusion 2314a extends laterally outward from the first end 2308a of the enclosure 2302. As previously discussed, in some aspects (not illustrated), an extrusion 2314 can extend laterally inward from the first end 2308a and/or second end 2308b, In some aspects, the extrusion 2314a forms a generally circular shape around the circular opening that receives the medication delivery device. The first end 2308a and second end 2308b can each include a seal 2316 (e.g., 2316a, 2316b) such as, for example, an O-ring. In some aspects, each seal 2316 is watertight when the enclosure 2302 is attached to the medication delivery device.

In some aspects, the enclosure 2302 defines a seam 2318, formed by portion 2302a and portion 2302b being joined together. In some aspects, the seam 2318 extends radially around a perimeter of the medication delivery device (e.g., needleless connector 10). In some aspects, the seam 2318 is generally perpendicular to a longitudinal axis of the enclosure 2302. The enclosure 2302 can include one or more connectors 2320 (e.g., tabs, recesses) such that portion 2302a can be coupled to portion 2302b to form the enclosure 2302.

In some aspects, the enclosure 2302 can include one or more alignment features 2321. The alignment features 2321 can indicate a position of alignment for portion 2302a and portion 2302b such that the portions 2302a, 2302b can be aligned while coupling them together to form the enclosure 2302. In some examples, aligning the alignment feature 2321 of portion 2302a and with the alignment feature 2321 of portion 2302b, causes the connectors 2320 (e.g., recesses) of portion 2302a to align with the connectors 2320 (e.g., tabs) of portion 2302b such that the portions 2302a, 2302b can be coupled together (as illustrated for example in FIGS. 24A-24E).

Referring to FIGS. 24A-24E, one aspect of an electrical contact sensor assembly 2300 is illustrated, in a perspective view, perspective view, top view, side view, and side view respectively. The electrical contact sensor assembly 2300 is attached to a medication delivery device (e.g., needleless connector 10).

Referring to FIGS. 25A-25D, one aspect of an electrical contact sensor assembly 2500 is illustrated in a perspective view, side view, perspective view, and side view, respectively, according to one embodiment of the present disclosure. The electrical contact sensor assembly 2500 (as illustrated for example in FIGS. 25A-25D) can have one or more same or similar features as the electrical contact sensor assembly 2300 (as illustrated for example in FIGS. 23A-23B). Due to the same or similar features, the reference numbers and corresponding descriptions provided for various components, elements, portions, etc., provided for the electrical contact sensor assembly 2300 in FIGS. 23A-23B can be generally applied to the same or similar components, elements, portions, etc., provided for the electrical contact sensor assembly 2500 in FIGS. 25A-25D; however, the reference numbers in FIGS. 25A-25D are 2500 series rather than 2300 series.

The electrical contact sensor assembly 2500 can be attached to a medication delivery device such as, for example, a needleless connector 10. Similar to the electrical contact sensor assembly 900 (as illustrated for example in FIGS. 9-10), the electrical contact sensor assembly 2500 (as illustrated for example in FIGS. 25A-25D) can be attached to other types of medication delivery devices and is not limited to a needleless connector 10. The electrical contact sensor assembly 2500 can be attached to the medication delivery device (e.g., needleless connector 10) to enclose at least a portion of the outer surface 16 of the medication delivery device. When attached to the medication delivery device, the electrical contact sensor assembly 2500 can indirectly monitor the state of fluid flow through the medication delivery device without contacting any fluid (e.g., medication) within (or flowing through) the medication delivery device.

Continuing with FIGS. 25A-25D, in some embodiments, when the enclosure 2502 (e.g., 2502*a*, 2502*b*) is attached to the needleless connector 10, the enclosure 2502 encloses a portion of the outer surface 16 of the needleless connector 10. In some aspects, the enclosure encloses a portion of the outer surface 16 of the needleless connector 10 in a longitudinal direction (e.g., along the longitudinal axis of the needleless connector 10). In some examples, the enclosure 2502 encloses a length of the outer surface 16 of the needleless connector 10 that is equal to the length between the ends 2508*a*, 2508*b* of the enclosure 2502.

In some aspects, the enclosure 2502 encloses a portion of the outer surface 16 of the needleless connector 10 in a radial direction (e.g., around a perimeter of the outer surface 16 of the needleless connector 10). In some examples, the enclosure 2502 can extend 360-degrees (as illustrated for example by the enclosure 2402 of the electrical contact sensor assembly 2400 illustrated in FIGS. 24A-24E) around the perimeter of the outer surface 16 of the needleless connector 10. In other examples, the enclosure 2502 extends less than 360-degrees around the perimeter (as illustrated for example by the enclosure 2502 of the electrical contact sensor assembly 2500 illustrated in FIGS. 25A-25D) of the outer surface 16 of the needleless connector 10. For example, the enclosure 2502 can define an angle A that enclosure 2502 does not enclose around the perimeter of the outer surface 16 of the needleless connector 10, as illustrated in the side views in FIG. 25B and FIG. 25D.

In some examples, the angle A is greater than 0-degrees such that the enclosure extends less than 360-degrees around the perimeter of the outer surface 16 of the needleless connector 10. In some examples, the angle A is greater than 10-degrees such that the enclosure extends less than 350-degrees around the perimeter of the outer surface 16 of the needleless connector 10. In some examples, the angle A is greater than 20-degrees such that the enclosure extends less than 340-degrees around the perimeter of the outer surface 16 of the needleless connector 10. In some examples, the angle A is greater than 30-degrees such that the enclosure extends less than 330-degrees around the perimeter of the outer surface 16 of the needleless connector 10. In some examples, the angle A is greater than 40-degrees such that the enclosure extends less than 320-degrees around the perimeter of the outer surface 16 of the needleless connector 10. In some examples, the angle A is greater than 50-degrees such that the enclosure extends less than 310-degrees around the perimeter of the outer surface 16 of the needleless connector 10. In some examples, the angle A is greater than 60-degrees such that the enclosure extends less than 300-degrees around the perimeter of the outer surface 16 of the needleless connector 10.

Referring to FIGS. 26A-26D, a needleless connector 10 is illustrated in a perspective view, a perspective view, a top view, and a side view, respectively. The needleless connector 10 extends from a first end 12 to a second end 14 and defines an outer surface 16. The needleless connector 10 is configured for fluid (e.g., medication) to flow therethrough. Thus, the needleless connector 10 can be connected within a medication flow path such that fluid can pass through the inside of the needleless connector 10. The needleless connector 10 can be positioned within an electrical contact sensor assembly, such as electrical contact sensor assembly 900 (as illustrated for example in FIG. 11), electrical contact sensor assembly 2300 (as illustrated for example in FIGS. 24A-24E), and/or electrical contact sensor assembly 2500 (as illustrated for example in FIGS. 25A-25D).

In some aspects, the needleless connector 10 can be used to connect the electrical contact sensor assembly 900 with the IV medication pathway (i.e., the fluid flow path of an IV line). The needleless connector 10 includes a first end 12 and a second end 14 that are configured to connect to the IV medication pathway. In one embodiment, the first end 12 of the needleless connector 10 is configured to connect to a catheter. The second end 14 of the needleless connector 10 contains a generally cylindrical shape that defines an exterior curved surface, and the exterior curved surface contains a threaded structure.

In one embodiment, the electrical contact sensor assembly 900 attaches around the needleless connector 10 that is within the medication flow path. In one example, the enclosure of the electrical contact sensor assembly 900 encloses a portion of the needleless connector 10. For example, the first end and/or second end of the needleless connector 10 can extend beyond the first end 908*a* and/or the second end 908*b* of the enclosure 902. In other examples, the enclosure of the electrical contact sensor assembly 900 can enclose the entirety of the needleless connector 10.

Figure 27A:
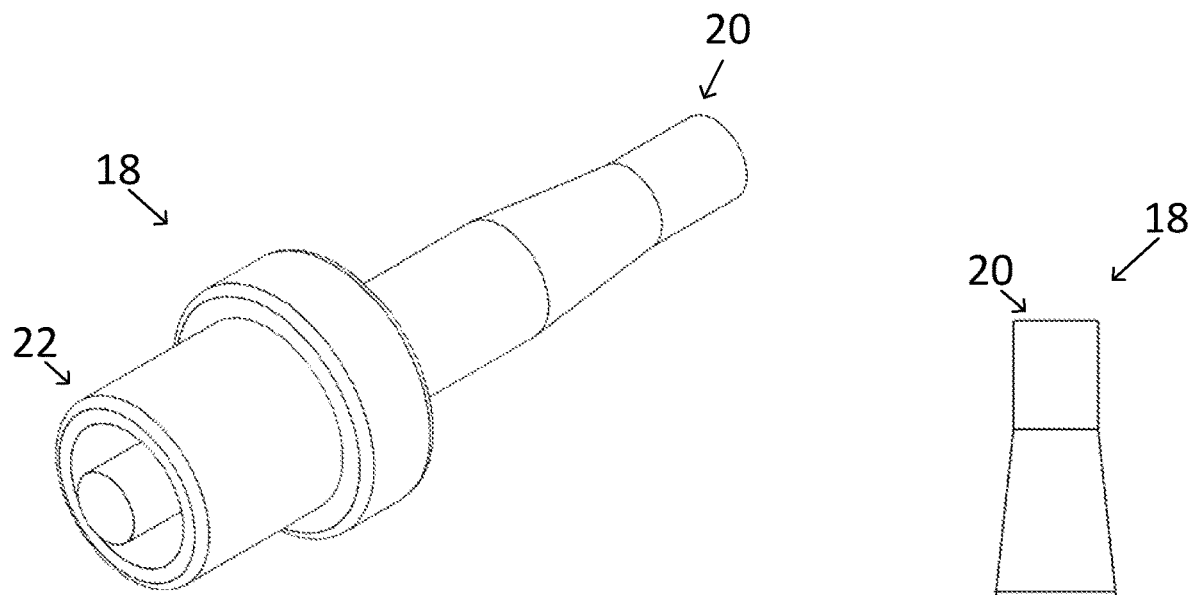
FIGS. 27A-27C illustrate a pump connector in a perspective view, top view, and side view, respectively.
Figure 27B:
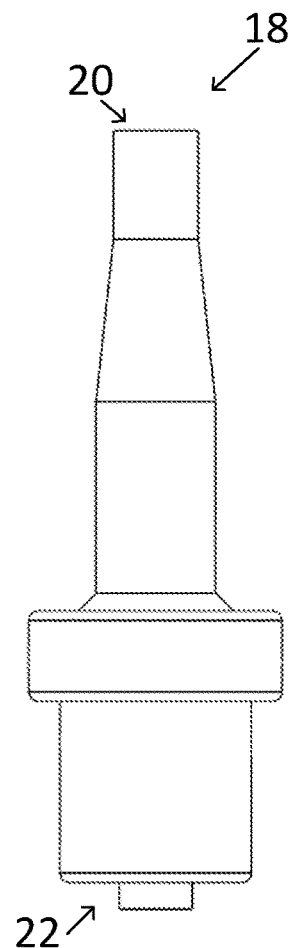
Figure 27C:
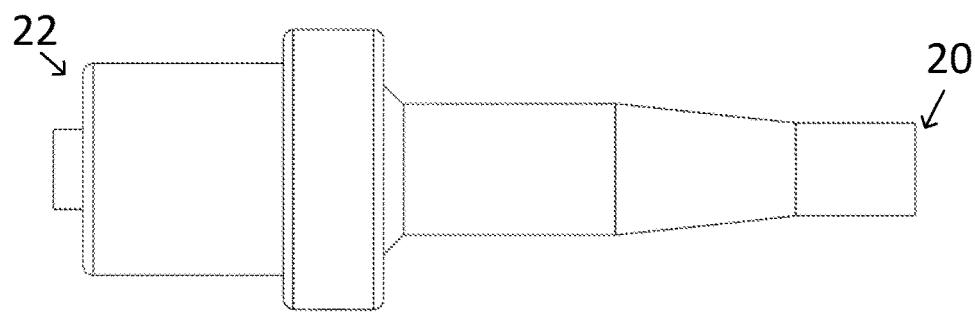

Referring to FIGS. 27A-27C, a pump connector 18 is illustrated in a perspective view, a top view, and a side view, respectively, according to one embodiment of the present disclosure. The pump connector 18 extends from a first end 20 to a second end 22. The pump connector 18 is configured for fluid (e.g., medication) to flow therethrough. Thus, the pump connector 18 can be connected within a medication flow path such that fluid (e.g., medication) can pass through the inside of the pump connector 18. In one embodiment, the second end 22 of the pump connector 18 can be coupled (e.g., removably coupled) to the first end 12 of the needleless connector 10, as illustrated for example in FIG. 10, such that the pump connector 18 is in fluid communication with the needleless connector 10.

In some aspects, the pump connector 18 can be used to connect the electrical contact sensor assembly 900 with the IV medication pathway (i.e., the fluid flow path of an IV line). The pump connector 18 can contain a first end 20 and a second end 22 that each are configured to connect to the IV medication pathway. In one embodiment, the second end 22 of the pump connector 18 contains a generally cylindrical opening that defines an interior curved surface. The diameter of the interior curved surface can be slightly larger than the diameter of the exterior curved surface of the first end 12 of the needleless connector 10. Additionally, the interior curved surface of the pump connector 18 may contain a threaded structure that is configured to engage with the threaded structure on the exterior curved surface of the first end 12 of the needleless connector 10. The first end 22 of the pump connector 18 can be configured to connect to a catheter.

In one embodiment, the pump connector 18 is incorporated into the medication flow path such that fluid (e.g., medication) can flow therethrough. In other embodiments, the fluid flow pathway can include a connector that includes any fitting that is appropriate for use with a medication delivery device. For example, the connector can be a luer taper fitting.

Figure 28A:
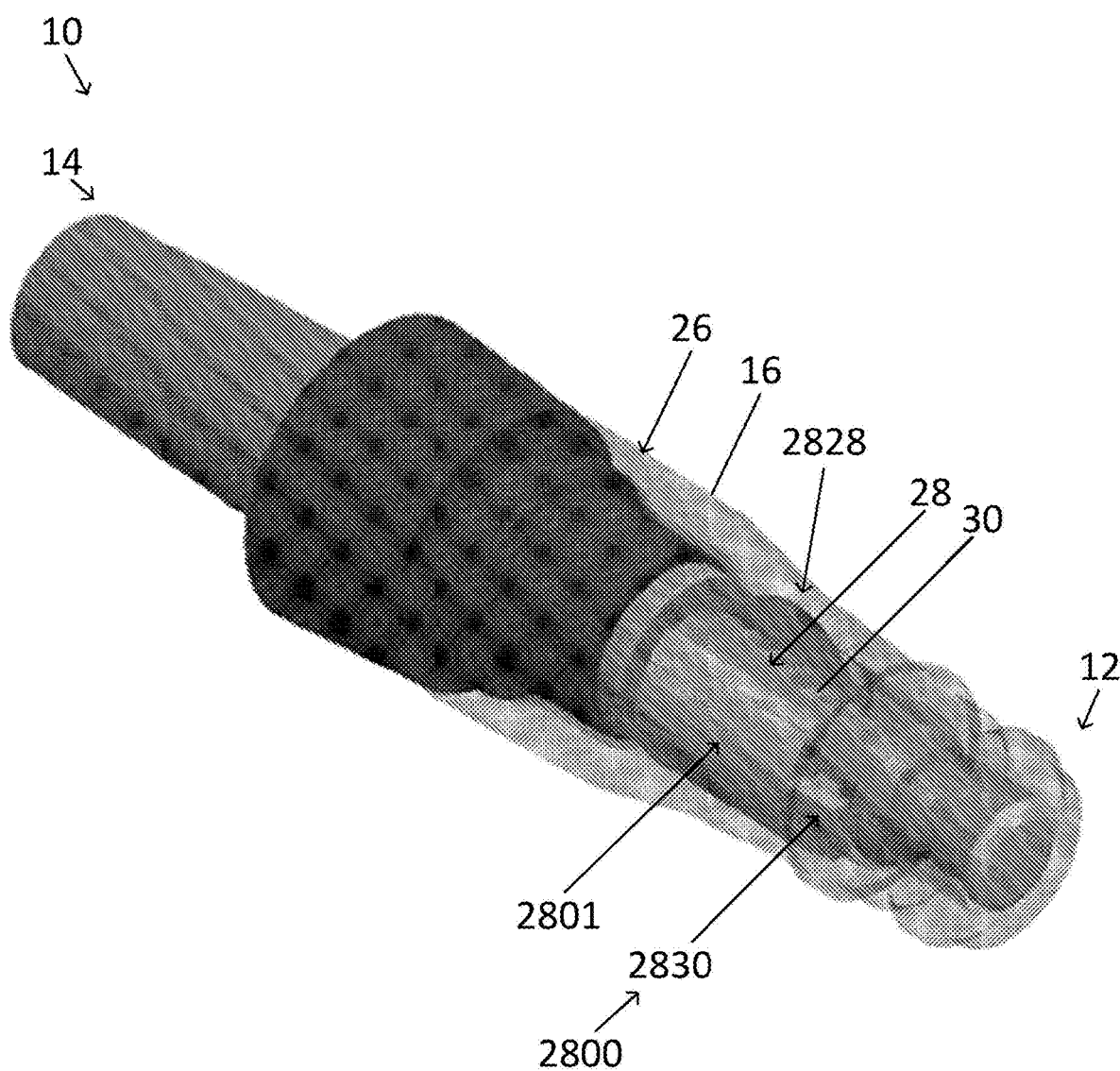
FIGS. 28A-28C illustrate an electrical contact sensor incorporated into a needleless connector in a perspective view, cross-sectional perspective view, and cross-sectional side view, respectively, according to one embodiment of the present disclosure.
Figure 28B:
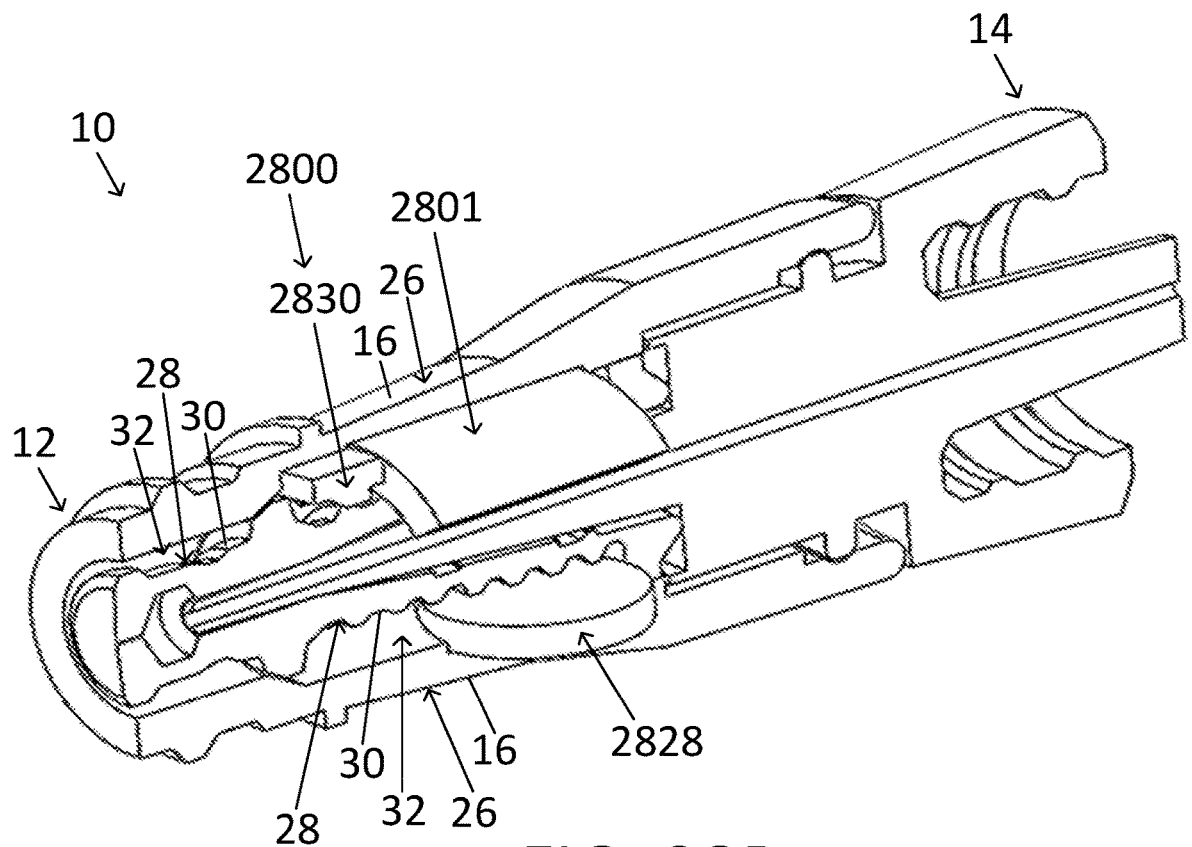
Figure 28C:
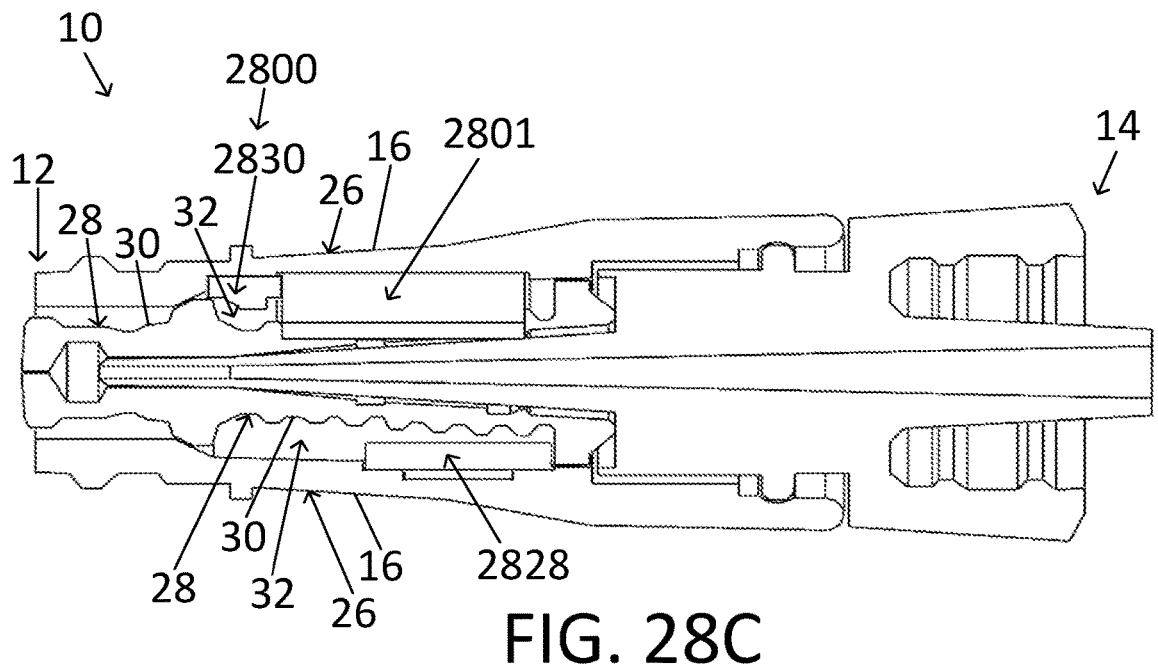

Referring to FIG. 28A-28C, one aspect of an electrical contact sensor assembly 2800 that is incorporated within a needleless connector 10 is illustrated in a perspective view, cross-sectional perspective view, and cross-sectional side view, respectively. The electrical contact sensor assembly 2800 (as illustrated for example in FIGS. 28A-28C) can have one or more same or similar features as the electrical contact sensor assembly 2300 (as illustrated for example in FIGS. 23A-23B). Due to the same or similar features, the reference numbers and corresponding descriptions provided for various components, elements, portions, etc., provided for the electrical contact sensor assembly 2300 in FIGS. 23A-23B can be generally applied to the same or similar components, elements, portions, etc., provided for the electrical contact sensor assembly 2800 in FIGS. 28A-28C; however, the reference numbers in FIGS. 28A-28C are 2800 series rather than 2300 series.

The needleless connector 10 can include an outer shell 26, which encloses a compressible sleeve 28. In some aspects, the outer shell 26 defines an outer surface 16. In some aspects, the compressible sleeve 28 defines an outer surface 30. A cavity 32 is located between the outer shell 26 and the compressible sleeve 28 of the needleless connector 10.

In some embodiments, an electrical contact sensor assembly 2800 can be integrated within the needleless connector 10. For example, the electrical contact sensor assembly 2800 can be disposed within the cavity 32 such that the electrical contact sensor assembly 2800. In some aspects, the electrical contact sensor assembly 2800 is enclosed within the outer shell 26 of the needleless connector 10. In some aspects, the electrical contact sensor assembly 2800 is around the compressible sleeve 28 (e.g., outer surface 30 of the compressible sleeve 28) of the needleless connector 10.

In some embodiments, the electrical contact sensor assembly 2800 includes a contact sensor 2830, electronics 2801, and a battery 2828 disposed within the cavity. In some aspects, the electronics 2801 (as illustrated for example in FIGS. 28A-28C) can include the same or similar components as the flexible PCB assembly 904 and/or the rigid PCB assembly 906 (as illustrated for example in FIGS. 9-10 and discussed above). The electronics 2801 (e.g., controlled) are in communication with the contact sensor 2830 and are operable to relay the state of electrical connection (e.g., electrically connected, not electrically connected) of the contact sensor 2830.

The contact sensor 2830 can be oriented such that the contact sensor 2830 is actuated (e.g., depressed) when a component of a fluid flow path is connected to the first end 12 of the needleless connector 10. In some aspects, connecting a component to the first end 12 of the needleless connector 10 causes the compressible sleeve 28 to compress within the needleless connector 10. In some embodiments, the compression of the compressible sleeve 28 causes the contact sensor 2830 to actuate (e.g., transition from an undepressed position to a depressed position). In this manner, the state of electrical connection (e.g., electrically connected, not electrically connected) of the contact sensor 2830 corresponds to the state of connection (e.g., connected, not connected) of the needleless connector 10. In other embodiments, the compression of the compressible sleeve 28 can actuate the contact sensor 2830 by other means, including but not limited to: pulling on the sensor, breaking or distorting an electrical signal or pathway.

The present disclosure includes a method for using the electrical contact sensor assembly 900 to indirectly monitor a state of fluid flow (e.g., flow, no flow) through a medication delivery device (e.g., needleless connector 10). It should be noted that the method can be applied to electrical contact sensor assembly 900 (as illustrated for example in FIG. 11), electrical contact sensor assembly 2300 (as illustrated for example in FIGS. 24A-24E), and/or electrical contact sensor assembly 2500 (as illustrated for example in FIGS. 25A-25D).

The electrical contact sensor assembly 900 (e.g., enclosure 902) can be attached around the medication delivery device to enclose at least a portion of the outer surface of the medication delivery device. For example, the electrical contact sensor assembly 900 can be attached around a needleless connector 10 to enclose at least a portion of the outer surface 16 of the needleless connector 10. The enclosure 902 can include a contact sensor 930 and a controller disposed therein. The electrical contact sensor assembly 900 (e.g., the controller) can relay a state of electrical connection of the contact sensor 930.

A patient dashboard may be operable to display the information collected and/or stored from the electrical contact sensor assembly 900. The patient dashboard may be operated as a webpage. The dashboard may be configured to collect patient data and present easily actionable items. The patient data may or may not be encrypted. In some embodiments, the patient data may be replaced with placeholders for the sake of confidentiality. For example, the dashboard may display serial numbers instead of the name of the patient. The hospital database may store the patient's name and patient serial number, wherein the hospital is responsible for security of patient-specific information.

The patient dashboard may include multiple versions that are specific to different types of dashboard users. The different versions may be based on the level and amount of data that each user should be able to access. For example, the dashboard may include a patient version for patient's that are undergoing treatment. Separately, the dashboard may include a provider version for doctors and/or nurses treating the patient.

The patient dashboard may be configured to empower the workflow of the healthcare providers. The dashboard may allow the provider to filter patients based on their most recent adherence reports. Criteria to filter may be based on comparisons to the prescribed medication treatment plan and/or the number of recorded treatments. Comparisons to the prescribed medication treatment plan may include the number of connections and disconnections of the device, the amount of time the fluid flow path is complete, the spacing between treatment times and between connection or disconnection events. For an example regarding the number of connections and disconnections of the device, when patients do the SASH (Saline-Antibiotics-Saline-Heparin) protocol, which involves 4 separate infusions in a row, too many or too few connections and disconnections means they did not do this protocol correctly.

Based on the criteria above, the patient dashboard may be configured display the data in an easy to understand and easy to use format. For example, the format may include one or more graphs. The graphs may or may not have various markings, such as lines, to indicate greater specificity. The format may also use various colors to indicate levels of severity and/or need for attention.

The patient dashboard may generate various reports. For example, the dashboard may generate daily reports for providers. The dashboard settings may be configured so that the daily reports are automatically sent at a specific time. As another example, the dashboard may generate reports for specific patients if a certain threshold of error or concern is reached. The dashboard settings may be configured so that the provider may preset one or more specific thresholds.

The patient dashboard may contain one or more virtual tabs or pages. As a first example, the dashboard may include an overall patient view, which displays all patients, information about the patients, and information about the behavior of each patient. The overall patient view may require specific credentials, such as a provider, that authorizes the user to see the overall patient view. As a second example, the dashboard may include a patient specific dashboard, which displaces instances of usage, the trends of patient usages, and other relevant data for the interested party.

As a third example, the dashboard may include a patient schedule view, which displays the schedule of the patient and the long-term adherence of the patient. As a fourth example, the dashboard may include a change schedule, which allows the provider to update the schedule of each patient as necessary. The change schedule view may require specific credentials, such as a provider, that authorizes the user to see the change schedule view. If the schedule of the patient is updated through the change schedule view, the patient specific dashboard may correspondingly update.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred aspects(s) thereof, the articles "a", "an", "the" and "said" are intended to mean that there are one or more of the elements. The terms "comprising", "including" and "having" are intended to be inclusive and mean that there may be additional elements other than the listed elements.

As used herein, the terms "communication" and "communicate" may refer to the reception, receipt, transmission, transfer, provision, and/or the like, of information (e.g., data, signals, messages, instructions, commands, and/or the like). For one unit (e.g., a device, a system, a component of a device or system, combinations thereof, and/or the like) to be in communication with another unit means that the one unit is able to directly or indirectly receive information from and/or transmit information to the other unit. This may refer to a direct or indirect connection (e.g., a direct communication connection, an indirect communication connection, and/or the like) that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively transmit information to the second unit. Alternatively, a first unit may be in communication with a second unit if at least one intermediary unit (e.g., a third unit located between the first unit and the second unit) processes information received from the first unit and communicates the processed information to the second unit.

As used herein, the term "computing device" may refer to one or more electronic devices that are operable to directly or indirectly communicate with or over one or more networks. The computing device may be a mobile device. As used herein, the term "mobile device" may refer to one or more portable electronic devices operable to communicate with one or more networks. As an example, a mobile device may include a cellular phone (e.g., a smartphone or standard cellular phone), a portable computer (e.g., a tablet computer, a laptop computer, etc.), a wearable device (e.g., a watch, pair of glasses, lens, clothing, and/or the like), a portable computer with no user interface, a personal digital assistant (PDA), and/or other like devices. The computing device may not be a mobile device, such as a desktop computer. Furthermore, the term "computer" may refer to any computing device that includes the necessary components to receive, process, and output data, and normally includes a display, a processor, a memory, an input device, and a network interface.

As used herein, the term "application" or "application program interface" (API) refers to computer code, a set of rules, or other data sorted on a computer-readable medium that may be executed by a processor to facilitate interaction between software components, such as a client-side front-end and/or server-side back-end for receiving data from the client. An "interface" refers to a generated display, such as one or more graphical user interfaces (GUIs) with which a user may interact, either directly or indirectly (e.g., through a keyboard, mouse, etc.).

As used herein, the term "medication" refers to any substance (in liquid form) that is used to treat a health condition experienced by the patient. Non-limiting examples of medication include chemo drugs, nutrition delivered in total parenteral nutrition (TPN), hemotherapy drugs such as doxorubicin, vincristine, cisplatin, and paclitaxel, antibiotics such as vancomycin, meropenem, and gentamicin, antifungal drugs such as micafungin and amphotericin, pain medications such as hydromorphone and morphine, drugs for low blood pressure such as dopamine, epinephrine, norepinephrine, and dobutamine, and immunoglobulin medications (IVIG).

As used herein, the terms "attached" or "coupled" can be used interchangeably and are defined as connected, whether directly or indirectly through intervening components, and are not necessarily limited to physical connections. The connection can be such that the objects are permanently connected or releasably connected.

As various changes could be made in the above-described systems without departing from the scope of the invention, it is intended that all matter contained in the above description and in the examples given below, shall be interpreted as illustrative and not in a limiting sense.

What is claimed is:

1. A system for indirectly monitoring a state of fluid flow by monitoring a state of connection of a medication delivery device, the system comprising:
   an enclosure configured to attach around at least a portion of an outer surface of the medication delivery device such that at least a portion of the outer surface of the medication delivery device is enclosed within the enclosure;
   a contact sensor comprising an actuator, the contact sensor disposed within the enclosure and configured to monitor a state of electrical connection; and
   a controller disposed within the enclosure, the controller in communication with the contact sensor and configured to relay the state of electrical connection, wherein the state of electrical connection of the contact sensor corresponds to the state of connection of the medication delivery device, wherein the enclosure has a first end and a second end opposite the first end, wherein the first end of the enclosure is compressible such that at least a portion of first end is configured to compress towards the contact sensor when the medication delivery device transitions to a connected position, and wherein the actuator is in communication with the first end of the enclosure.

2. The system of claim 1, wherein the state of connection of the medication delivery device corresponds to the state of fluid flow.

3. The system of claim 1, wherein the state of connection of the medication delivery device corresponds to a state of connection of a medication flow pathway.

4. The system of claim 3, wherein the state of connection of the medication flow pathway corresponds to the state of fluid flow.

5. The system of claim 1, wherein the system indirectly monitors the state of fluid flow without contacting any fluid within the medication delivery device.

6. The system of claim 1, wherein the enclosure encloses 360-degrees radially around a perimeter of the outer surface of the medication delivery device when the enclosure is attached thereto.

7. The system of claim 1, wherein the enclosure encloses less than 360-degrees radially around a perimeter of the outer surface of the medication delivery device when the enclosure is attached thereto.

8. The system of claim 1, wherein the enclosure encloses a length along the outer surface of the medication delivery device when the enclosure is attached thereto, wherein the length is less than or equal to a distance between the first end and the second end of the enclosure.

9. The system of claim 8, wherein the enclosure encloses 360-degrees radially around a perimeter of the outer surface of the medication delivery device.

10. The system of claim 8, wherein the enclosure encloses less than 360-degrees radially around a perimeter of the outer surface of the medication delivery device.

11. The system of claim 1, wherein the medication delivery device is a needleless connector.

12. The system of claim 11, wherein the outer surface is defined by a compressible sleeve within the needleless connector such that the system is integrated within the needleless connector.

13. The system of claim 11, wherein the outer surface is defined by an outer component of the needleless connector such that the system is external to the needleless connector.

14. The system of claim 1, wherein the medication delivery device is fluidly connected within a medication flow pathway that includes one or more of the following: a medication source, an injection site, an IV insertion line, an extension set, an extension line, a regulator, or an end piece.

15. The system of claim 1, wherein the enclosure is configured to non-removably attach around at least a portion of the outer surface of the medication delivery device.

16. The system of claim 1, wherein the enclosure includes a first portion and a second portion, wherein the first portion is configured to attach to the second portion to attach the enclosure around at least a portion of the outer surface of the medication delivery device.

17. The system of claim 1, wherein connecting the medication delivery device to a fluid flow path causes the first end of the enclosure to compress, wherein the actuator depresses and causes a change of the state of electrical connection of the contact sensor when the first end of the enclosure compresses.

18. The system of claim 1, wherein the medication delivery device is a needleless connector and the enclosure is integrated with the needleless connector.

19. The system of claim 1, wherein the first end includes one or more extrusions extending outward, the one or more extrusions configured to contact a surface of a connector when the medication delivery device is in a connected position.

20. The system of claim 1, wherein the first end includes one or more extrusions extending inward, the one or more extrusions configured to contact a surface of the contact sensor when the medication delivery device is in a connected position.

21. The system of claim 1, wherein the first end defines a first seal that abuts the outer surface of the medication delivery device, wherein the second end defines a second seal that abuts the outer surface of the medication delivery device, wherein the first seal and the second seal are each water-tight.

22. The system of claim 1, wherein the enclosure includes one or more structures configured to abut the outer surface of the medication delivery device, wherein the one or more structures abutting the medication delivery device inhibit translation and rotation of the medication delivery device with respect to the enclosure.

23. The system of claim 1, wherein an outer surface of the enclosure includes one or more surface features, the one or more surface features being parallel to an axis of the enclosure and defining a gripping surface.

24. The system of claim 1, further comprising a battery disposed within the enclosure and in electrical communication with the contact sensor, wherein the battery is configured to supply a current that flows through the contact sensor when the contact sensor transitions to a closed-circuit position.

25. The system of claim 1, wherein the controller relays a change in the state of the electrical connection, wherein a change in the state of electrical connection corresponds a change in the state of fluid flow.

26. The system of claim 1, wherein the controller is configured to relay feedback to an authorized user, wherein the feedback includes if data was relayed by the controller, if the data matches a therapy regimen, if an action is suggested or a combination thereof.

27. The system of claim 1, further comprising an indicator configured to indicate a compliance status of the system, wherein the indicator is one or more of the following: a light integrated into the enclosure, a speaker disposed within the enclosure, a vibrator disposed within the enclosure.

28. A system for indirectly monitoring a state of fluid flow by monitoring a state of connection of a medication delivery device, the system comprising:

an enclosure configured to attach around at least a portion of an outer surface of the medication delivery device such that at least a portion of the outer surface of the medication delivery device is enclosed within the enclosure;

a contact sensor disposed within the enclosure, the contact sensor configured to monitor a state of electrical connection; and a controller disposed within the enclosure, the controller in communication with the contact sensor and configured to relay the state of electrical connection, wherein the state of electrical connection of the contact sensor corresponds to the state of connection of the medication delivery device, and wherein the enclosure has a first end and a second end opposite the first end, wherein the first end includes one or more extrusions extending inward, the one or more extrusions configured to contact a surface of the contact sensor when the medication delivery device is in a connected position.

29. A system for indirectly monitoring a state of fluid flow by monitoring a state of connection of a medication delivery device, the system comprising:

an enclosure configured to attach around at least a portion of an outer surface of the medication delivery device such that at least a portion of the outer surface of the medication delivery device is enclosed within the enclosure;

a contact sensor disposed within the enclosure, the contact sensor configured to monitor a state of electrical connection; and a controller disposed within the enclosure, the controller in communication with the contact sensor and configured to relay the state of electrical connection, wherein the state of electrical connection of the contact sensor corresponds to the state of connection of the medication delivery device, and wherein the enclosure has a first end and a second end opposite the first end, wherein the first end defines a first seal that abuts the outer surface of the medication delivery device, wherein the second end defines a second seal that abuts the outer surface of the medication delivery device, wherein the first seal and the second seal are each water-tight.

* * * * *